US011550391B2

(12) United States Patent
Yoo et al.

(10) Patent No.: US 11,550,391 B2
(45) Date of Patent: Jan. 10, 2023

(54) SYSTEMS AND METHODS FOR CONTROLLING A DEVICE USING DETECTED CHANGES IN A NEURAL-RELATED SIGNAL

(71) Applicant: Synchron Australia Pty Limited, Melbourne (AU)

(72) Inventors: Peter Eli Yoo, West Melbourne (AU); Thomas James Oxley, New York, NY (US)

(73) Assignee: Synchron Australia Pty Limited, Melbourne (AU)

(*) Notice: Subject to any disclaimer, the term of this patent is extended or adjusted under 35 U.S.C. 154(b) by 0 days.

(21) Appl. No.: 17/397,651

(22) Filed: Aug. 9, 2021

(65) Prior Publication Data

US 2021/0365117 A1 Nov. 25, 2021

Related U.S. Application Data

(63) Continuation of application No. PCT/US2021/025440, filed on Apr. 1, 2021.

(60) Provisional application No. 63/003,480, filed on Apr. 1, 2020.

(51) Int. Cl.
*G06F 3/01* (2006.01)
*A61B 5/00* (2006.01)

(52) U.S. Cl.
CPC ............ *G06F 3/015* (2013.01); *A61B 5/6876* (2013.01)

(58) Field of Classification Search
CPC ......... A61B 5/283; A61B 5/24; A61B 5/0215; A61B 5/6862
See application file for complete search history.

(56) References Cited

U.S. PATENT DOCUMENTS

| | | | | |
|---|---|---|---|---|
| 8,805,494 | B2* | 8/2014 | Libbus | A61N 1/3987 607/2 |
| 10,575,783 | B2* | 3/2020 | Oxley | A61N 1/3787 |
| 2006/0189900 | A1* | 8/2006 | Flaherty | G06N 3/061 600/595 |
| 2007/0032738 | A1* | 2/2007 | Flaherty | A61B 5/375 600/545 |
| 2011/0307029 | A1* | 12/2011 | Hargrove | A61N 1/0456 607/45 |
| 2012/0172743 | A1 | 7/2012 | Aguilar et al. | |
| 2012/0296476 | A1* | 11/2012 | Cale | G05B 15/02 700/275 |
| 2014/0309538 | A1* | 10/2014 | More | A61B 5/7221 600/300 |
| 2015/0038869 | A1* | 2/2015 | Simon | A61B 5/377 702/85 |
| 2015/0272465 | A1* | 10/2015 | Ishii | A61B 5/7445 600/545 |

(Continued)

*Primary Examiner* — William Lu
(74) *Attorney, Agent, or Firm* — Levine Bagade Han LLP

(57) ABSTRACT

Systems and methods of controlling a device using detected changes in a neural-related signal of a subject are disclosed. In one embodiment, a method of controlling a device or software application comprises detecting a first change in a neural-related signal of a subject, detecting a second change in the neural-related signal, and transmitting an input command to the device upon or following the detection of the second change in the neural-related signal. The neural-related signal can be detected using a neural interface implanted within a brain of the subject.

19 Claims, 13 Drawing Sheets

(56) References Cited

U.S. PATENT DOCUMENTS

| | | | | |
|---|---|---|---|---|
| 2015/0313496 A1* | 11/2015 | Connor | ........... | A61B 5/369 |
| | | | | 600/301 |
| 2015/0317817 A1* | 11/2015 | Ryu | ........... | G09B 19/06 |
| | | | | 345/471 |
| 2015/0338917 A1* | 11/2015 | Steiner | ........... | H04L 9/3271 |
| | | | | 345/156 |
| 2015/0351655 A1* | 12/2015 | Coleman | ........... | A61B 5/375 |
| | | | | 600/595 |
| 2016/0242690 A1* | 8/2016 | Principe | ........... | A61B 5/316 |
| 2018/0178009 A1* | 6/2018 | Lee | ........... | A61N 1/36025 |
| 2018/0292902 A1* | 10/2018 | Min | ........... | A61B 5/375 |
| 2018/0303595 A1* | 10/2018 | Opie | ........... | A61B 5/283 |
| 2019/0038438 A1 | 2/2019 | John et al. | | |
| 2019/0058703 A1* | 2/2019 | Zhu | ........... | A61B 5/374 |
| 2019/0104968 A1 | 4/2019 | Fedele | | |
| 2019/0113973 A1* | 4/2019 | Coleman | ........... | H04L 12/16 |
| 2019/0166434 A1* | 5/2019 | Petley | ........... | H04R 25/30 |
| 2020/0061378 A1* | 2/2020 | Ganguly | ........... | A61B 5/4047 |
| 2020/0363869 A1* | 11/2020 | Yoo | ........... | A61B 5/24 |
| 2021/0361222 A1* | 11/2021 | Elbogen | ........... | A61B 5/374 |

\* cited by examiner

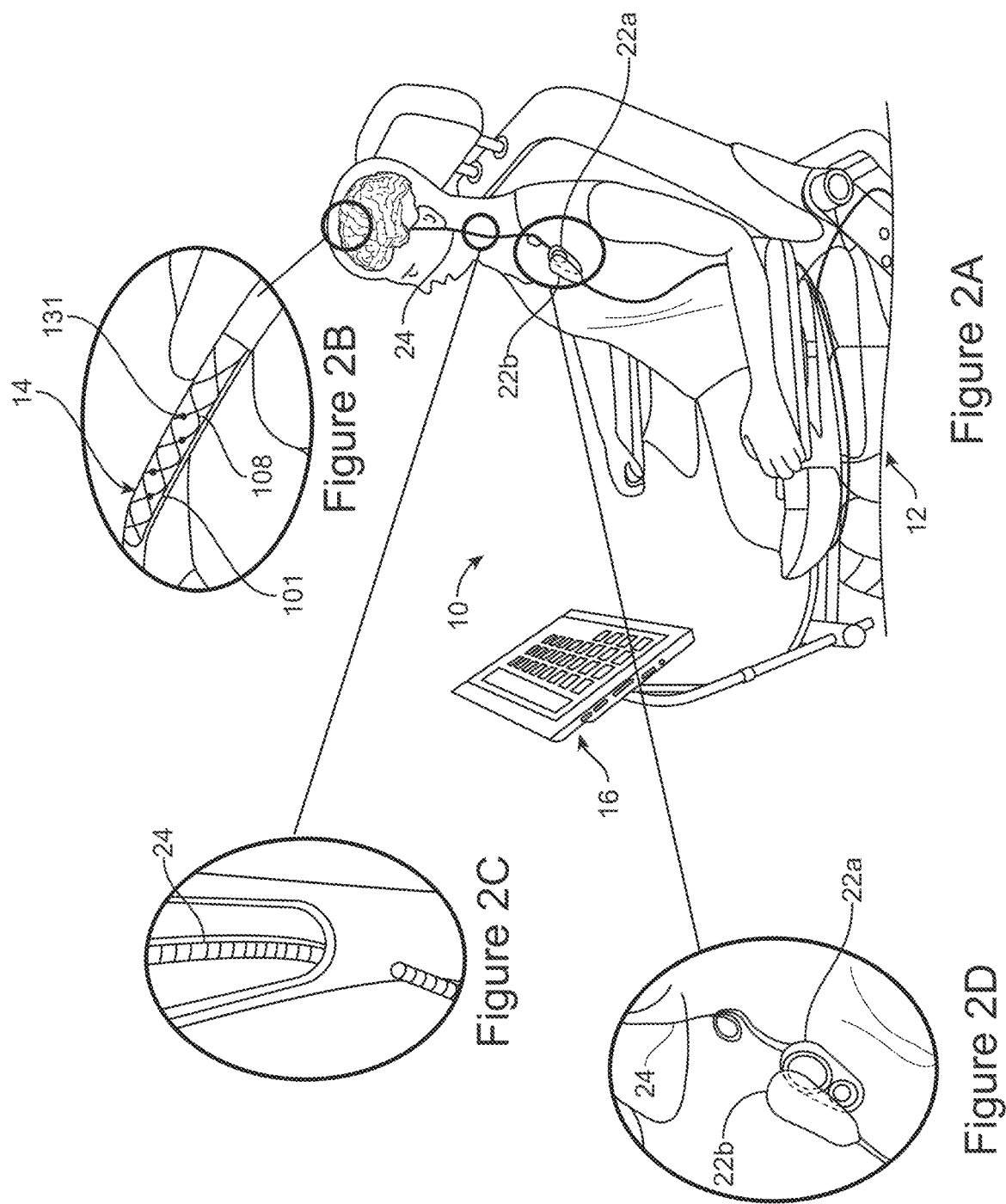

Change in power of beta-band and gamma-band frequencies when subject conjures and subsequently releases a thought concerning movement of the subject's left ankle
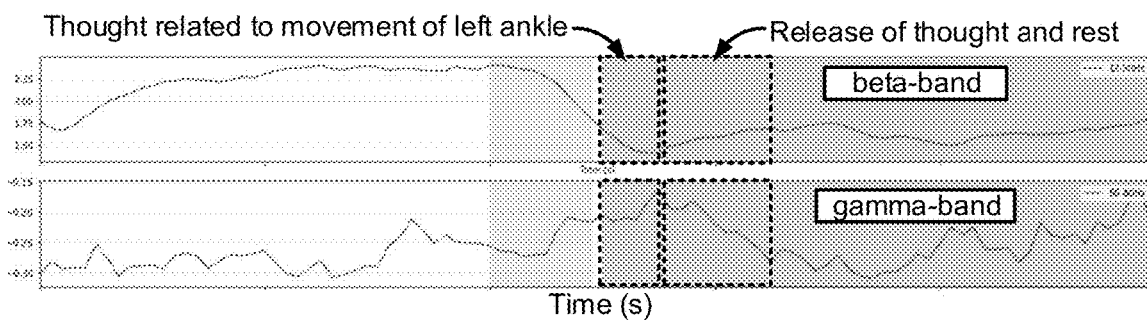
Change in power of beta-band and gamma-band frequencies when subject conjures and subsequently releases a thought concerning movement of the subject's right ankle
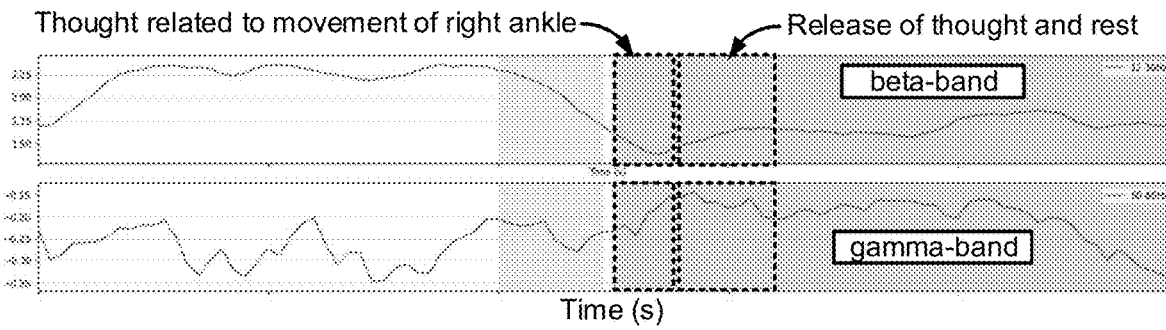
FIG. 14

SYSTEMS AND METHODS FOR CONTROLLING A DEVICE USING DETECTED CHANGES IN A NEURAL-RELATED SIGNAL

CROSS-REFERENCE TO RELATED APPLICATION

This application is a continuation of International Patent Application No. PCT/US2021/025440 filed on Apr. 1, 2021, which claims the benefit of U.S. Provisional Application No. 63/003,480 filed on Apr. 1, 2020, the contents of which are hereby incorporated by reference in their entireties.

TECHNICAL FIELD

This disclosure relates generally to brain computer interfaces and, more specifically, to systems and methods of controlling a device using detected changes in a neural-related signal of a subject.

BACKGROUND

Previously, it has been shown that people with mobility limitations can use brain computer interfaces (BCIs) to control peripherals such as personal electronic devices, internet of things (IoT) devices, software, and mobility vehicles. An effective BCI should allow the entire spectrum of people with mobility limitations to effectively control such peripherals, including those with severe mobility limitations such as locked-in patients that may only have control over a single switch or virtual switch through the BCI.

However, current BCIs that allow such locked-in patients to access peripherals through a single switch often use automatic switch scanning to affect such controls. Automatic switch scanning involves serially scanning through numerous interactive items on a given control panel where the user selects one target item by engaging the switch while the target item is highlighted. This method is tedious and unforgiving when an erroneous selection is made as the user must wait for the serial scanning to finish before restarting the entire process again to correct the selection.

Moreover, locked-in patients may also have difficulty engaging even the single virtual switch since current BCI systems often rely on neural-related signals that are difficult to detect or may present false positives.

Therefore, a solution is needed which allows a patient with severe mobility limitations to maintain or retain their independence even when such patients only have control over a single virtual switch. Such a solution should not be overly complicated and should address the shortcomings of current BCI systems and methods.

SUMMARY

Systems and methods of controlling a device using detected changes in a neural-related signal of a subject are disclosed. In one embodiment, a method of controlling a device or software application is disclosed. The method can comprise detecting a reduction in an intensity of a neural-related signal of a subject below a baseline level measured, detecting an increase in the intensity of the neural-related signal beyond the baseline level following the reduction, and transmitting an input command to the device upon or following the detection of the increase in the intensity of the neural-related signal.

In some embodiments, the neural-related signal of the subject can be a neural oscillation or brainwave of the subject. The neural oscillation can comprise oscillations at one or more frequency bands. In certain embodiments, the neural oscillation comprises a beta-band oscillation at a frequency of between about 12 Hz to 30 Hz.

In some embodiments, the neural-related signal can be measured or monitored using an endovascular device implanted within the subject. In these and other embodiments, the steps of detecting the reduction or increase in the intensity of the neural-related signal and transmitting the input command can be performed using one or more processors of an apparatus separate from the endovascular device or one or more processors of an apparatus embedded within or coupled to the endovascular device.

In some embodiments, the apparatus can be configured to be located extracorporeally or outside the body of the subject. In other embodiments, the apparatus can be configured to be implanted within the subject (e.g., within a pectoral region or arm of the subject).

The apparatus can refer to a telemetry unit and/or a host device. In other embodiment, the apparatus can refer to a computing device or a controller/control unit of an implantable or non-implantable device.

The neural-related signal can be detected via electrodes of the endovascular device implanted within the subject. For example, the neural-related signal can be detected via electrodes of the endovascular device implanted within the brain of the subject.

The method can further comprise filtering, using the one or more processors, raw neural-related signals obtained from the endovascular device using one or more software filters. The method can also comprise feeding filtered signals into a classification layer of software run on the apparatus or another device. The classification layer is configured to automatically detect the reduction and increase in the intensity of the neural-related signal using a machine learning classifier.

In some embodiments, detecting the reduction in the intensity of the neural-related signal can comprise detecting a decrease in the power of the neural oscillation below a baseline oscillation power level. For example, the reduction in the intensity of the neural-related signal below the baseline level measured can be referred to as a desynchronization of the neural-related signal. The reduction in the intensity of the neural-related signal can be caused by the subject conjuring and holding a task-relevant thought or a task-irrelevant thought.

In these and other embodiments, detecting the increase in the intensity of the neural-related signal can comprise detecting an increase in the power of the neural oscillation beyond a baseline oscillation power level. For example, the increase in the intensity of the neural-related signal beyond the baseline level measured can be referred to as a rebound of the neural-related signal. The increase in the intensity of the neural-related signal can be caused by the subject mentally releasing the task-relevant thought or the task-irrelevant thought.

The task-irrelevant thought can be a thought related to a body function of the subject, such as the subject holding a thought to contract a hamstring muscle of the subject.

The method can further comprise providing at least one of a visual feedback, an auditory feedback, a tactile feedback, and feedback in the form of neural stimulation to the subject after transmitting the input command to the device.

Transmitting the input command can comprise transmitting the input command to one or more end applications run on the device. The input command can be a command to the device to accomplish at least part of a task associated with the task-relevant thought.

The device can be at least one of a personal computing device (e.g., a laptop, a mobile phone, and/or a tablet computer) or an internet-of-things (IoT) device (e.g., a smart light switch, refrigerator, oven, and/or washing machine). In some embodiments, the device can be a mobility vehicle such as a wheelchair.

Another method of controlling a device or software application is disclosed. The method can comprise detecting a reduction in an intensity of a neural-related signal of a subject below a baseline level measured, detecting an increase in the intensity of the neural-related signal beyond the baseline level following the reduction, determining a duration of the reduction in the intensity of the neural-related signal, selecting an input command from a plurality of conditional input commands based on the duration, and transmitting the input command selected to the device.

In some embodiments, selecting the input command based on the duration can comprise comparing the duration with one or more temporal thresholds associated with the conditional input commands and selecting the input command from the plurality of conditional input commands based on whether the duration exceeds or fails to reach the one or more temporal thresholds. The duration of the reduction in the intensity of the neural-related signal can be an amount of time a thought is held by the subject.

In some embodiments, the neural-related signal of the subject can be a neural oscillation or brainwave of the subject. The neural oscillation can comprise oscillations at one or more frequency bands. In certain embodiments, the neural oscillation comprises a beta-band oscillation at a frequency of between about 12 Hz to 30 Hz.

In some embodiments, the neural-related signal can be measured or monitored using an endovascular device implanted within the subject. In these and other embodiments, the steps of detecting the reduction or increase in the intensity of the neural-related signal, determining a duration of the reduction in the intensity of the neural-related signal, selecting an input command from a plurality of conditional input commands based on the duration, and transmitting the input command selected to the device can be performed using one or more processors of an apparatus separate from the endovascular device or one or more processors of an apparatus embedded within or coupled to the endovascular device.

In some embodiments, the apparatus can be configured to be located extracorporeally or outside the body of the subject. In other embodiments, the apparatus can be configured to be implanted within the subject (e.g., within a pectoral region or arm of the subject).

The apparatus can refer to a telemetry unit and/or a host device. In other embodiment, the apparatus can refer to a computing device or a controller/control unit of an implantable or non-implantable device.

The neural-related signal can be detected via electrodes of the endovascular device implanted within the subject. For example, the neural-related signal can be detected via electrodes of the endovascular device implanted within the brain of the subject.

The method can further comprise filtering, using the one or more processors, raw neural-related signals obtained from the endovascular device using one or more software filters. The method can also comprise feeding filtered signals into a classification layer of software run on the apparatus or another device. The classification layer is configured to automatically detect the reduction and increase in the intensity of the neural-related signal using a machine learning classifier.

In some embodiments, detecting the reduction in the intensity of the neural-related signal can comprise detecting a decrease in the power of the neural oscillation below a baseline oscillation power level. For example, the reduction in the intensity of the neural-related signal below the baseline level measured can be referred to as a desynchronization of the neural-related signal. The reduction in the intensity of the neural-related signal can be caused by the subject conjuring and holding a task-relevant thought or a task-irrelevant thought.

In these and other embodiments, detecting the increase in the intensity of the neural-related signal can comprise detecting an increase in the power of the neural oscillation beyond a baseline oscillation power level. For example, the increase in the intensity of the neural-related signal beyond the baseline level measured can be referred to as a rebound of the neural-related signal. The increase in the intensity of the neural-related signal can be caused by the subject mentally releasing the task-relevant thought or the task-irrelevant thought. The task-irrelevant thought can be a thought related to a body function of the subject, such as the subject holding a thought to contract a hamstring muscle of the subject.

The method can further comprise providing at least one of a visual feedback, an auditory feedback, a tactile feedback, and feedback in the form of neural stimulation to the subject concerning the input command selected prior to transmitting the input command to the device.

Transmitting the input command can comprise transmitting the input command to one or more end applications run on the device. The input command can be a command to the device to accomplish at least part of a task associated with the task-relevant thought.

The device can be at least one of a personal computing device (e.g., a laptop, a mobile phone, and/or a tablet computer) or an internet-of-things (IoT) device (e.g., a smart light switch, refrigerator, oven, and/or washing machine). In some embodiments, the device can be a mobility vehicle such as a wheelchair.

Another method of controlling a device or software application is disclosed. The method can comprise detecting a first change in a neural-related signal of a subject, detecting a second change in the neural-related signal, and transmitting an input command to the device upon or following the detection of the second change in the neural-related signal.

The method can further comprise determining a duration of the first change in the neural-related signal and using the duration to select the input command from a plurality of conditional input commands based on the duration. The method can further comprise providing at least one of a visual feedback, an auditory feedback, a tactile feedback, and feedback in the form of neural stimulation to the subject concerning the input command selected.

In some embodiments, the first change can be a reduction in an intensity of the neural-related signal below a baseline signal level. In these embodiments, the second change can be an increase in the intensity of the neural-related signal beyond the baseline signal level. Moreover, in these embodiments, the first change can be produced when the subject generates and holds a thought and the second change can be produced when the subject generates and holds a second thought.

In other embodiments, the first change can be an increase in an intensity of the neural-related signal beyond a baseline signal level. In these embodiments, the second change can be a decrease in the intensity of the neural-related signal below the baseline signal level. Moreover, in these embodiments, the first change can be produced when the subject generates and holds a thought and the second change can be produced when the subject generates and holds a second thought. Alternatively, the first change can be produced when the subject mentally releases a first thought and the second change can be produced when the subject generates and holds a second thought.

In some embodiments, the thought can be a task-relevant thought. In other embodiments, the thought can be a task-irrelevant thought. The thought can be related to a body function of the subject.

The change in the neural-related signal can be detected via an endovascular device implanted within the subject. In these and other embodiments, the steps of detecting the first change in the neural-related signal, detecting the second change in the neural-related signal, determining a duration of the change(s) in the neural-related signal, selecting an input command from a plurality of conditional input commands based on the duration, and transmitting the input command selected to the device can be performed using one or more processors of an apparatus separate from the endovascular device or one or more processors of an apparatus embedded within or coupled to the endovascular device.

In some embodiments, the apparatus can be configured to be located extracorporeally or outside the body of the subject. In other embodiments, the apparatus can be configured to be implanted within the subject (e.g., within a pectoral region or arm of the subject).

The apparatus can refer to a telemetry unit and/or a host device. In other embodiment, the apparatus can refer to a computing device or a controller/control unit of an implantable or non-implantable device.

The neural-related signal can be detected via electrodes of the endovascular device implanted within the subject. For example, the neural-related signal can be detected via electrodes of the endovascular device implanted within the brain of the subject.

The method can further comprise filtering, using the one or more processors, raw neural-related signals obtained from the endovascular device using one or more software filters. The method can also comprise feeding filtered signals into a classification layer of software run on the apparatus or another device. The classification layer is configured to automatically detect the reduction and increase in the intensity of the neural-related signal using a machine learning classifier.

A system for controlling a device is also disclosed. The system can comprise an endovascular device configured to measure or monitor a neural-related signal of a subject and an apparatus comprising one or more processors. The one or more processors can be programmed to detect a reduction in an intensity of the neural-related signal of a subject below a baseline level measured, detect an increase in the intensity of the neural-related signal beyond the baseline level following the reduction, and transmit an input command to the device upon or following the detection of the increase in the intensity of the neural-related signal.

In some embodiments, the one or more processors can be programmed to detect a reduction in an intensity of the neural-related signal of a subject below a baseline level measured, detect an increase in the intensity of the neural-related signal beyond the baseline level following the reduction, determine a duration of the reduction in the intensity of the neural-related signal, select an input command from a plurality of conditional input commands based on the duration, and transmit the input command selected to the device.

The one or more processors can be further programmed to compare the duration with one or more temporal thresholds associated with the conditional input commands and select the input command from the plurality of conditional input commands based on whether the duration exceeds or fails to reach the one or more temporal thresholds.

The neural-related signal of the subject can be a neural oscillation of the subject. For example, the one or more processors can be programmed to detect the reduction in the intensity of the neural-related signal by detecting a decrease in the power of the neural oscillation below a baseline oscillation power level. The one or more processors can also be programmed to detect the increase in the intensity of the neural-related signal by detecting an increase in the power of the neural oscillation beyond a baseline oscillation power level.

The neural oscillation can comprise oscillations at one or more frequency bands. For example, the neural oscillation can comprise a beta-band oscillation at a frequency of between about 12 Hz to 30 Hz.

In some embodiments, the reduction in the intensity of the neural-related signal can be caused by the subject conjuring and holding a task-relevant thought. In these embodiments, the increase in the intensity of the neural-related signal can be caused by the subject mentally releasing the task-relevant thought. The input command can be a command to the device to accomplish at least part of a task associated with the task-relevant thought.

In other embodiments, the reduction in the intensity of the neural-related signal can be caused by the subject conjuring and holding a task-irrelevant thought. The increase in the intensity of the neural-related signal can be caused by the subject mentally releasing the task-irrelevant thought. The input command can be a command to the device to accomplish at least part of a task not associated with the task-irrelevant thought. For example, the task-irrelevant thought can be a thought related to a body function of the subject.

In certain embodiments, the reduction in the intensity of the neural-related signal below the baseline level measured can be considered a desynchronization of the neural-related signal. In these embodiments, the increase in the intensity of the neural-related signal beyond the baseline level measured can be considered a rebound of the neural-related signal.

The endovascular device can be configured to be implanted within the brain of the subject. For example, the endovascular device can be configured to be implanted within a vein or sinus of the subject. The neural-related signal can be measured or monitored using electrodes of the endovascular device implanted within the subject.

In some embodiments, the apparatus can be configured to be located extracorporeally of the subject. In other embodiments, the apparatus can be configured to be implanted within the subject.

The one or more processors can be further programmed to filter raw neural-related signals obtained from the endovascular device using one or more software filters. The one or more processors can be further programmed to feed filtered signals into a classification layer to automatically detect the reduction and increase in the intensity of the neural-related signal using a machine learning classifier.

The one or more processors can be further programmed to provide at least one of a visual feedback, an auditory feedback, and a tactile feedback to the subject concerning the input command. In these and other embodiments, the endovascular device can be configured to provide a feedback in the form of neural stimulation to the subject concerning the input command.

The one or more processors can be further programmed to transmit the input command to one or more end applications run on the device. In some embodiments, device can be at least one of a personal computing device (e.g., a laptop, a mobile phone, and/or a tablet computer) or an internet-of-things (IoT) device (e.g., a smart light switch, refrigerator, oven, and/or washing machine). In other embodiments, the device can be a mobility vehicle such as a wheelchair.

A system for controlling a device can comprise an endovascular device configured to measure or monitor a neural-related signal of a subject and an apparatus configured to detect changes in the neural-related signal.

In some embodiments, the apparatus can comprise one or more processors programmed to detect a first change in the neural-related signal of the subject, detect a second change in the neural-related signal, and transmit an input command to the device upon or following the detection of the second change in the neural-related signal.

The one or more processors can be further programmed to determine a duration of the first change in the neural-related signal and use the duration to select the input command from a plurality of conditional input commands based on the duration.

In some embodiments, the first change can be a reduction in an intensity of the neural-related signal below a baseline signal level. In these embodiments, the second change can be an increase in the intensity of the neural-related signal beyond the baseline signal level.

In other embodiments, the first change can be an increase in an intensity of the neural-related signal beyond a baseline signal level. In these embodiments, the second change can be a decrease in the intensity of the neural-related signal below the baseline signal level.

For example, the first change can be produced when the subject generates and holds a thought. The second change can be produced when the subject mentally releases the thought.

Alternatively, the first change can be produced when the subject mentally releases a first thought and the second change can be produced when the subject generates and holds a second thought.

BRIEF DESCRIPTION OF THE DRAWINGS

The drawings shown and described are exemplary embodiments and non-limiting. Like reference numerals indicate identical or functionally equivalent features throughout.

FIGS. 2A-2D illustrate a variation of a universal switch model in communication with an end application.

FIG. 14 illustrates changes in the power of the beta-band (e.g., 12 Hz to 30 Hz) and gamma-band (e.g., 60 Hz to 80 Hz) frequencies as the subject conjures/holds and subsequently releases thoughts concerning movement of the subject's left and right ankles.

DETAILED DESCRIPTION

Figure 1A:
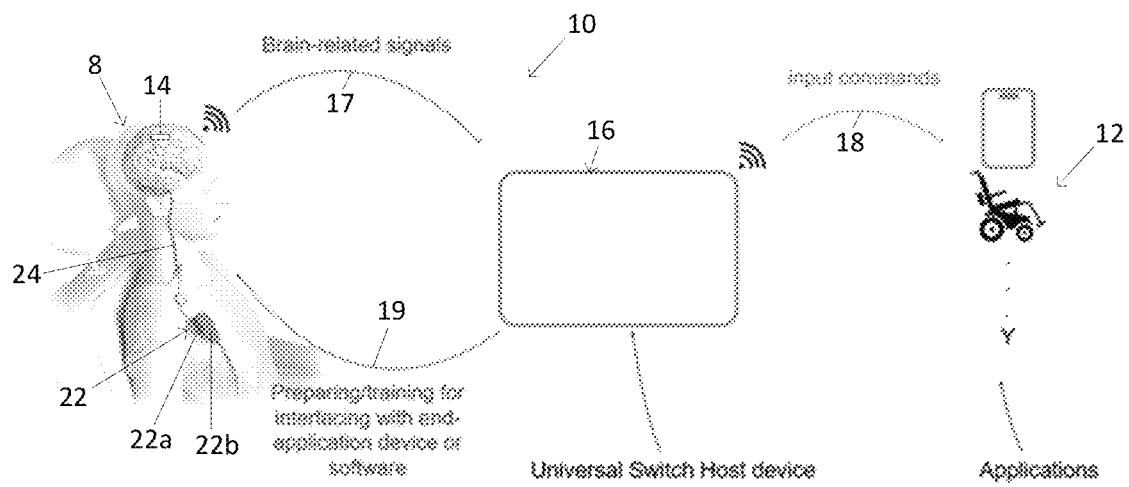
FIG. 1A illustrates a variation of a universal switch module.
Figure 1B:
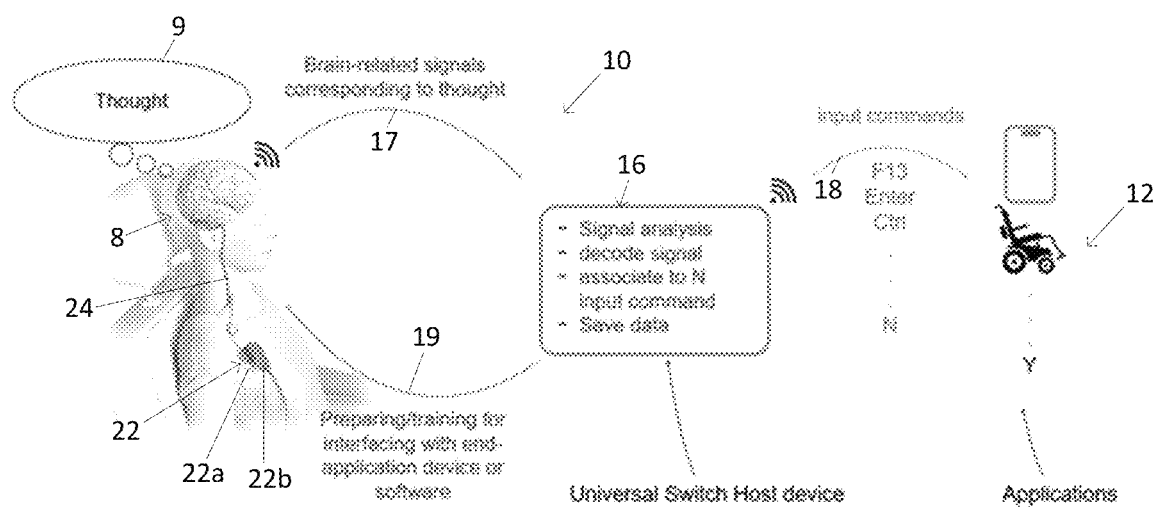
FIG. 1B illustrates a variation of the universal switch module of FIG. 1A when the patient is thinking of a thought.
Figure 1C:
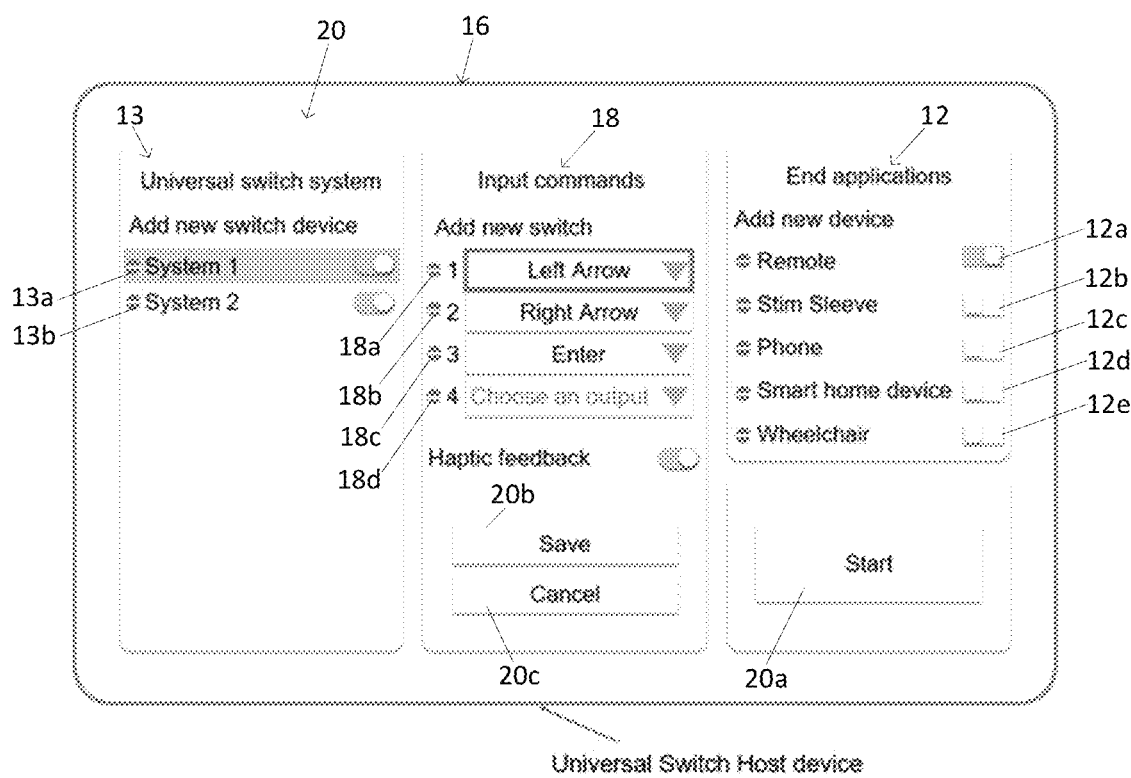
FIG. 1C illustrates a variation of a user interface of a host device of the universal switch module of FIGS. 1A and 1B.

Universal switch modules, universal switches, and methods of using the same are disclosed. For example, FIGS. 1A-1C illustrate a variation of a universal switch module 10 that a patient 8 (e.g., BCI user) can use to control one or multiple end applications 12 by thinking of a thought 9. The module 10 can include a neural interface 14 and a host device 16. The module 10 (e.g., the host device 16) can be in wired and/or wireless communication with the one or multiple end applications 12. The neural interface 14 can be a biological medium signal detector (e.g., an electrical conductor, a biochemical sensor), the host device 16 can be a computer (e.g., laptop, smartphone), and the end applications 12 can be any electronic device or software. The neural interface 14 can, via one or multiple sensors, monitor neural-related signals 17 of the biological medium. A processor of the module 10 can analyze the detected neural-related signals 17 to determine whether the detected neural-related signals 17 are associated with a thought 9 assigned to an input command 18 of an end application 12. When a thought 9 that is assigned to an input command 18 is detected by the neural interface 14 and associated with the input command 18 by the processor, the input command 18 can be sent (e.g., via the processor, a controller, or a transceiver) to the end application 12 that that input command 18 is associated with. The thought 9 can be assigned to input of commands 18 of multiple end applications 12. The module 10 thereby advantageously enables the patient 8 to independently control multiple end applications 12 with a single thought (e.g., the thought 9), for example, a first end application and a second end application, where the thought 9 can be used to control the first and second applications at different times and/or at the same time. In this way, the module 10 can function as a universal switch module, capable of using the same thought 9 to control multiple end applications 12 (e.g., software and devices). The thought 9 can be a universal switch, assignable to any input command 18 of any end application 12 (e.g., to an input command 18 of the first end application and to an input command 18 of the second end application). The first end application can be a first device or first software. The second end application can be a second device or second software.

When the patient 8 thinks of the thought 9, the input commands 18 that are associated with the thought 9 can be sent to their corresponding end applications 12 by the module 10 (e.g., via a processor, a controller, or a transceiver). For example, if the thought 9 is assigned to an input command 18 of the first end application, the input command 18 of the first end application can be sent to the first end application when the patient 8 thinks of the thought 9, and if the thought 9 is assigned to an input command 18 of the second end application, the input command 18 of the second end application can be sent to the second end application when the patient 8 thinks of the thought 9. The thought 9 can thereby interface with, or control, multiple end applications 12, such that the thought 9 can function like a universal button (e.g., the thought 9) on a universal controller (e.g., the patient's brain). Any number of thoughts 9 can be used as switches. The number of thoughts 9 used as switches can correspond to, for example, the number of controls (e.g., input commands 18) needed or desired to control an end application 12.

To use video game controllers as an example, the patient's thoughts 9 can be assigned to any input command 18 associated with any individual button, any button combination, and any directional movement (e.g., of a joystick, of a control pad such as a directional pad) of the controller, such that that the patient 8 can play any game of any video game system using their thoughts 9 with or without the presence of a conventional physical controller. Video game systems are just one example of end applications 12. The module 10 enables the thoughts 9 to be assigned to the input commands 18 of any end application 12 such that the patient's thoughts 9 can be mapped to the controls of any software or device. The module 10 can thereby organize the patient's thoughts 9 into a group of assignable switches, universal in nature, but specific in execution once assigned to an input command 18. Additional exemplary examples of end applications 12 include mobility devices (e.g., vehicles, wheelchairs, wheelchair lifts), prosthetic limbs (e.g., prosthetic arms, prosthetic legs), phones (e.g., smartphones), smart household appliances, and smart household systems.

The neural interface 14 can detect neural-related signals 17, including those associated with the thoughts 9 and those not associated with the thoughts 9. For example, the neural interface 14 can have one or multiple sensors that can detect (also referred to as obtain, sense, record, and measure) the neural-related signals 17, including those that are generated by a biological medium of the patient 8 when the patient 8 thinks of a thought 9, and including those that are generated by a biological medium of the patient 8 not associated with the thought 9 (e.g., form the patient responding to stimuli not associated with the thought 9). The sensors of the neural interface 14 can record signals from and/or stimulate a biological medium of the patient 8. The biological medium can be, for example, neural tissue, vascular tissue, blood, bone, muscle, cerebrospinal fluid, or any combination thereof. The sensors can be, for example, electrodes, where an electrode can be any electrical conductor for sensing electrical activity of the biological medium. The sensors can be, for example, biochemical sensors. The neural interface 14 can have a single type of sensor (e.g., only electrodes) or multiple types of sensors (e.g., one or multiple electrodes and one or multiple biochemical sensors).

The neural-related signals can be any signal (e.g., electrical, biochemical) detectable from the biological medium, can be any feature or features extracted from a detected neural-related signal (e.g., via a computer processor), or both, where extracted features can be or can include characteristic information about the thoughts 9 of the patient 8 so that different thoughts 9 can be distinguished from one another. As another example, the neural-related signals can be electrical signals, can be any signal (e.g., biochemical signal) caused by an electrical signal, can be any feature or features extracted from a detected neural-related signal (e.g., via a computer processor), or any combination thereof. The neural-related signals can be neural signals such as brainwaves. Where the biological medium is inside the patient's skull, the neural-related signals can be, for example, brain signals (e.g., detected from brain tissue) that result from or are caused by the patient 8 thinking of the thought 9. In this way, the neural-related signals can be brain-related signals such as electrical signals from any portion or portions of the patient's brain (e.g., motor cortex, sensory cortex). Where the biological medium is outside the patient's skull, the neural-related signals can be, for example, electrical signals associated with muscle contraction (e.g., of a body part such as an eyelid, an eye, the nose, an ear, a finger, an arm, a toe, a leg) that result from or are caused by the patient 8 thinking of the thought 9. The thoughts 9 (e.g., movement of a body part, a memory, a task) that the patient 8 thinks of when neural-related signals are being detected from their brain tissue can be the same or different than the thoughts 9 that the patient 8 thinks of when neural-related signals are being detected from non-brain tissue. The neural interface 14 can be positionable inside the patient's brain, outside the patient's brain, or both.

The module 10 can include one or multiple neural interfaces 14, for example, 1 to 10 or more neural interfaces 14, including every 1 neural interface increment within this range (e.g., 1 neural interface, 2 neural interfaces, 10 neural interfaces), where each neural interface 14 can have one or multiple sensors (e.g., electrodes) configured to detect neural-related signals (e.g., neural signals). The location of the neural interfaces 14 can be chosen to optimize the recording of the neural-related signals, for example, such as selecting the location where the signal is strongest, where interference from noise is minimized, where trauma to the patient 8 caused by implantation or engagement of the neural interface 14 to the patient 8 (e.g., via surgery) is minimized, or any combination thereof. For example, the neural interface 14 can be a brain machine interface such as an endovascular device (e.g., a stent) that has one or multiple electrodes for detecting electrical activity of the brain. Where multiple neural interfaces 14 are used, the neural interfaces 14 can be the same or different from one another. For example, where two neural interfaces 14 are used, both of the neural interfaces 14 can be an endovascular device having electrodes (e.g., an expandable and collapsible stent having electrodes), or one of the neural interfaces 14 can be an endovascular device having electrodes and the other of the two neural interfaces 14 can be a device having sensors that is different from an endovascular device having electrodes.

FIGS. 1A and 1B further illustrate that the module 10 can include a telemetry unit 22 adapted for communication with the neural interface 14 and a communication conduit 24 (e.g., a wire) for facilitating communications between the neural interface 14 and the telemetry unit 22. The host device 16 can be adapted for wired and/or wireless communication with the telemetry unit 22. The host device 16 can be in wired and/or wireless communication with the telemetry unit 22.

FIGS. 1A and 1B further illustrate that the telemetry unit 22 can include an internal telemetry unit 22a and an external telemetry unit 22b. The internal telemetry unit 22a can be in wired or wireless communication with the external telemetry unit 22b. For example, the external telemetry unit 22b can be wirelessly connected to the internal telemetry unit 22a across the patient's skin. The internal telemetry unit 22a can be in wireless or wired communication with the neural interface 14, and the neural interface 14 can be electrically connected to the internal telemetry unit 22a via the communication conduit 24. The communication conduit 24 can be, for example, a wire such as a stent lead.

The module 10 can have a processor (also referred to as a processing unit) that can analyze and decode the neural-related signals detected by the neural interface 14. The processor can be a computer processor (e.g., microprocessor). The processor can apply a mathematical algorithm or model to detect the neural-related signals corresponding to when the patient 8 generates the thought 9. For example, once a neural-related signal 17 is sensed by the neural interface 14, the processor can apply a mathematical algorithm or a mathematical model to detect, decode, and/or classify the sensed neural-related signal 17. As another example, once a neural-related signal 17 is sensed by the neural interface 14, the processor can apply a mathematical algorithm or a mathematical model to detect, decode, and/or classify the information in the sensed neural-related signal 17. Once the neural-related signal 17 detected by the neural interface 14 is processed by the processor, the processor can associate the processed information (e.g., the detected, decoded, and/or classified neural related signal 17 and/or the detected, decoded, and/or classified information of the sensed neural-related signal 17) to the input commands 18 of the end applications 12.

The neural interface 14, the host device 16, and/or the telemetry unit 22 can have the processor. As another example, the neural interface 14, the host device 16, and/or the telemetry unit 22 can have a processor (e.g., such as the processor described above). For example, the host device 16 can, via the processor, analyze and decode the neural-related signals 17 that are detected by the neural interface 14. The neural interface 14 can be in wired or wireless communication with the host device 16, and the host device 16 can be in wired or wireless communication with the end applications 12. As another example, the neural interface 14 can be in wired or wireless communication with the telemetry unit 22, the telemetry unit 22 can be in wired or wireless communication with the host device 16, and the host device 16 can be in wired or wireless communication with the end applications 12. Data can be passed from the neutral interface 14 to the telemetry unit 22, from the telemetry unit 22 to the host device 16, from the host device 16 to one or multiple end applications 12, or any combination thereof, for example, to detect a thought 9 and trigger an input command 18. As another example, data can be passed in the reverse order, for example, from one or multiple end applications 12 to the host device 16, from the host device 16 to the telemetry unit 22, from the telemetry unit 22 to the neural interface 14, or any combination thereof, for example, to stimulate the biological medium via one or more of the sensors. The data can be data collected or processed by the processor, including, for example, the neural-related signals and/or features extracted therefrom. Where data is flowing toward the sensors, for example, from the processor, the data can include stimulant instructions such that when the stimulant instructions are be processed by the neural interface 14, the sensors of the neural interface can stimulate the biological medium.

FIGS. 1A and 1B further illustrate that when the patient 8 thinks of a thought 9, a biological medium of the patient 8 (e.g., biological medium inside the skull, outside the skull, or both) can generate neural-related signals 17 that are detectable by the neural interface 14. The sensors of the neural interface 14 can detect the neural-related signals 17 associated with the thought 9 when the patient 8 thinks of the thought 9. The neural-related signals 17 associated with the thought 9, features extracted from these neural-related signals 17, or both can be assigned or associated with any input command 18 for any of the end applications 12 controllable with the universal switch module 10. Each of the detectable neural-related signals 17 and/or their extracted features can thereby advantageously function as a universal switch, assignable to any input command 18 for any end application 12. In this way, when a thought 9 is detected by the neural interface 14, the input command 18 associated with that thought 9 can be triggered and sent to the end application 12 that the triggered input command 18 is associated with.

For example, when a thought 9 is detected by the neural interface 14 (e.g., by way of a sensed neural-related signal 17), a processor can analyze (e.g., detect, decode, classify, or any combination thereof) the sensed neural-related signal 17 and associate the sensed neural-related signal 17 and/or features extracted therefrom with the corresponding assigned input commands 18. The processor can thereby determine whether or not the thought 9 (e.g., the sensed neural related signal 17 and/or features extracted therefrom) is associated with any of the input commands 18. Upon a determination that the thought 9 is associated with an input command 18, the processor or a controller can activate (also referred to as trigger) the input command 18. Once an input command 18 is triggered by the module 10 (e.g., by the processor or the controller of the host device 16), the triggered input command 18 can be sent to its corresponding end application 12 so that that end application 12 (e.g., wheelchair, prosthetic arm, smart household appliance such as a coffee machine) can be controlled with the triggered input command 18. Once the end application 12 receives the triggered input command 18, the end application 12 can execute the instruction or instructions of the input command 18 (e.g., move the wheelchair forward at 1 meter per second, pinch the thumb and index finger of the prosthetic arm together, turn on the smart coffee machine). Thus, upon a determination that a thought 9 (e.g., a sensed neural-related signal 17 and/or features extracted therefrom) is associated with an input command 18, the input command 18 can be sent to its corresponding end application 12.

The extracted features can be the components of the sensed neural-related signals 17, including, for example, patterns of voltage fluctuations in the sensed neural-related signals 17, fluctuations in power in a specific band of frequencies embedded within the sensed neural-related signals 17, or both. For example, the neural-related signals 17 can have a various range of oscillating frequencies that correspond with when the patient 8 thinks the thought 9. Specific bands of frequencies can contain specific information. For example, the high-band frequency (e.g., 65 Hz-150 Hz) can contain information that correlate with motor related thoughts, hence, features in this high-band frequency range can be used (e.g., extracted from or identified in the sensed neural-related signals 17) to classify and/or decode neural events (e.g., the thoughts 9).

The thought 9 can be a universal switch. The thought 9 can function (e.g., be used as) as a universal switch, where the thought 9 can be assigned to any input command 18, or vice versa. The thought 9—by way of the detectable neural-related signals 17 associated therewith and/or the features extractable therefrom—can be assigned or associated with any input command 18 for any of the end applications 12 controllable with the universal switch module 10. The patient 8 can activate a desired input command 18 by thinking of the thought 9 that is associated with the input command 18 that the patient 8 desires. For example, when a thought 9 (e.g., memory of the patient's 9th birthday party) that is assigned to a particular input command 18 (e.g., move a wheelchair forward) is detected by the neural interface 14, the processor (e.g., of the host device 16) can associate the neural-related signal 17 associated with that thought 9 (e.g., memory of 9th birthday party) and/or features extracted therefrom to the corresponding assigned input command 18 (e.g., move a wheelchair forward). When the detected neural-related signal (e.g., and/or extracted features associated therewith) are associated with an assigned input command 18, the host device 16 can, via the processor or a controller, send that input command 18 to the end application 12 that the input command 18 is associated with to control the end application 12 with the input command 18 that the patient 8 triggered by thinking of the thought 9.

Where the thought 9 is assigned to multiple end applications 12 and only one of the end applications 12 is active (e.g., powered on and/or running), the host device 16 can send the triggered input command 18 to the active end application 12. As another example, where the thought 9 is assigned to multiple end applications 12 and some of the end applications 12 are active (e.g., powered on or running) and some of the end applications 12 are inactive (e.g., powered off or in standby mode), the host device 16 can send the triggered input command 18 to both the active and inactive end applications 12. The active end applications 12 can execute the input command 18 when the input command 18 is received by the active end applications 12. The inactive end applications 12 can execute the input command 18 when the inactive applications 12 become active (e.g., are powered on or start running), or the input command 18 can be placed in a queue (e.g., by the module 16 or by the end application 12) to be executed when the inactive applications 12 become active. As yet another example, where the thought 9 is assigned to multiple end applications 12 and more than one of the end applications 12 is active (e.g., powered on and/or running), for example, a first end application and a second end application, the host device 16 can send the triggered input command 18 associated with the first end application to the first end application and can send the triggered input command 18 associated with the second end application to the second end application, or the module 10 can give the patient 8 a choice of which of the triggered input commands 18 the patient 8 would like to send (e.g., send only the triggered input command 18 associated with the first end application, send only the triggered input command 18 associated with the second end application, or send both of the triggered input commands 18).

The thought 9 can be any thought or combination of thoughts. For example, the thought 9 that the patient 8 thinks of can be a single thought, multiple thoughts, multiple thoughts in series, multiple thoughts simultaneously, thoughts having different durations, thoughts having different frequencies, thoughts in one or multiple orders, thoughts in one or multiple combinations, or any combination thereof. A thought 9 can be a task-relevant thought, a task-irrelevant thought, or both, where task-relevant thoughts are related to the intended task of the patient 8 and where the task-irrelevant thoughts are not related to the intended task of the patient 8. For example, the thought 9 can be of a first task and the patient 8 can think of the first task to complete a second task (also referred to as the intended task and target task), for example, by using the module 10. The first task can be the same or different from the second task. Where the first task is the same as the second task, the thought 9 can be a task-relevant thought. Where the first task is different from the second task, the thought 9 can be a task-irrelevant thought. For example, where the first task that the patient 8 thinks of is moving a body limb (e.g., arm, leg) and the second task is the same as the first task, namely, moving a body limb (e.g., arm, leg), for example, of a prosthetic body limb, the thought 9 (e.g., of the first task) can be a task-relevant thought. The prosthetic body limb can be, for example, the end application 12 that the patient 8 is controlling with the thought 9. For example, for a task-relevant thought, the patient 8 can think of moving a cursor when the target task is to move a cursor. In contrast, for a task-irrelevant thought 9, where the patient 8 thinks of moving a body limb (e.g., arm) as the first task, the second task can be any task different from the first task of moving a body limb (e.g., arm) such that the second task can be a task of any end application 12 that is different from the first task. For example, for a task-irrelevant thought, the patient 8 can think of moving a body part (e.g., their hand) to the right when the target task is to move a cursor to the right. The patient 8 can thereby think of the first task (e.g., thought 9) to accomplish any second task, where the second task can be the same or different from the first task. The second task can be any task of any end application 12. For example, the second task can be any input command 18 of any end application 12. The thought 9 (e.g., the first task) can be assignable to any second task. The thought 9 (e.g., the first task) can be assigned to any second task. The patient 8 can thereby think of the first task to trigger any input command 18 (e.g., any second task) of any end application 12. The first task can thereby advantageously function as a universal switch. Each thought 9 can produce a repeatable neural-related signal detectable by the neural interface 14 (e.g., the detectable neural-related signals 17). Each detectable neural-related signal and/or features extractable therefrom can be a switch. The switch can be activated (also referred to as triggered), for example, when the patient 8 thinks of the thought 9 and the sensor detects that the switch is activated and/or the processor determines that one or multiple extracted features from the detected neural-related signal are present. The switch can be a universal switch, assignable and re-assignable to any input command 18, for example, to any set of input commands Input commands 18 can be added to, removed from, and/or modified from any set of input commands. For example, each end application 12 can have a set of input commands 18 associated therewith to which the neural-related signals 17 of the thoughts 9 can be assigned to.

Some of the thoughts 9 can be task-irrelevant thoughts (e.g., the patient 8 tries moving their hand to move a cursor to the right), some of the thoughts 9 can be task-relevant thoughts (e.g., the patient 8 tries moving a cursor when the target task is to move a cursor), some of the thoughts 9 can be both a task-irrelevant thought and a task-relevant thought, or any combination thereof. Where a thought 9 is both a task-irrelevant thought and a task-relevant thought, the thought 9 can be used as both a both a task-irrelevant thought (e.g., the patient 8 tries moving their hand to move a cursor to the right) and a task-relevant thought (e.g., the patient tries moving a cursor when the target task is to move a cursor) such that the thought 9 can be associated with multiple input commands 18, where one or multiple of those input commands 18 can be task-relevant to the thought 9 and where one or multiple of those input commands 18 can be task-irrelevant to the thought 9.

In this way, the thought 9 can be a universal switch assignable to any input command 18 for any end application 12, where each thought 9 can be assigned to one or multiple end applications 12. The module 10 advantageously enables each patient 8 to use their thoughts 9 like buttons on a controller (e.g., video game controller, any control interface) to control any end application 12 that the patient 8 would like. For example, a thought 9 can be assigned to each input command 18 of an end application 12, and the assigned input commands 18 can be used in any combination, like buttons on a controller, to control the end application 12. For example, where an end application 12 has four input commands 18 (e.g., like four buttons on a controller—a first input command, a second input command, a third input command, and a fourth input command), a different thought 9 can be assigned to each of the four input commands 18 (e.g., a first thought 9 can be assigned to the first input command 18, a second thought 9 can be assigned to the second input command 18, a third thought 9 can be assigned to the third input command 18, and a fourth thought 9 can be assigned to the fourth input command 18) such that the patient 8 can use these four thoughts 9 to activate the four input commands 18 and combinations thereof (e.g., any order, number, frequency, and duration of the four input commands 18) to control the end application 12. For example, for an end application 12 having four input commands 18, the four input commands 18 can be used to control the end application 12 using any combination of the four thoughts 9 assigned to the first, second, third, and fourth input commands 18, including, for example, a single activation of each input command by itself, multiple activations of each input command by itself (e.g., two activations in less than 5 second, three activations in less than 10 seconds), a combination of multiple input commands 18 (e.g., the first and second input command simultaneously or in series), or in any combination thereof. Like each individual thought 9, each combination of thoughts 9 can function as a universal switch. The patient 8 can control multiple end applications 12 with the first, second, third, and fourth thoughts 9. For example, the first thought 9 can be assigned to a first input command 18 of a first end application 12, the first thought 9 can be assigned to a first input command 18 of a second end application 12, the second thought 9 can be assigned to a second input command 18 of the first end application 12, the second thought 9 can be assigned to a second input command 18 of the second end application 12, the third thought 9 can be assigned to a third input command 18 of the first end application 12, the third thought 9 can be assigned to a third input command 18 of the second end application 12, the fourth thought 9 can be assigned to a fourth input command 18 of the first end application 12, the fourth thought 9 can be assigned to a fourth input command 18 of the second end application 12, or any combination thereof. For example, the first thought 9 can be assigned to a first input command 18 of a first end application 12 and to a first input command 18 of a second end application 12, the second thought 9 can be assigned to a second input command 18 of the first end application 12 and to a second input command 18 of the second end application 12, the third thought 9 can be assigned to a third input command 18 of the first end application 12 and to a third input command 18 of the second end application 12, the fourth thought 9 can be assigned to a fourth input command 18 of the first end application 12 and to a fourth input command 18 of the second end application 12, or any combination thereof. The first, second, third, and fourth thoughts 9 can be assigned to any application 12 (e.g., to first and second end applications). Some thoughts may only be assigned to single application 12 and some thoughts may be assigned to multiple applications 12. Even where a thought 9 is only assigned to a single application 12, the thought that is only assigned to one application 12 can be assignable to multiple applications 12 such that the patient 8 can take advantage of the universal applicability of the thought 9 (e.g., that is assigned to only one end application 12) on an as needed or as desired basis. As another example, all thoughts 9 may be assigned to multiple end applications 12.

The function of each input command 18 or combination of input commands for an end application 12 can be defined by the patient 8. As another example, the function of each input command 18 or combination of input commands for an end application 12 can be defined by the end application 12, such that third parties can plug into and have their end application input commands 18 assignable (also referred to as mappable) to a patient's set or subset of repeatable thoughts 9. This can advantageously allow third party programs to be more accessible to and tailor to the differing desires, needs, and capabilities of different patients 8. The module 10 can advantageously be an application programming interface (API) that third parties can interface with and which allows the thoughts 9 of patients 8 to be assigned and reassigned to various input commands 18, where, as described herein, each input command 18 can be activated by the patient 8 thinking of the thought 9 that is assigned to the input command 18 that the patient 8 wants to activate.

A patient's thoughts 9 can be assigned to the input commands 18 of an end application 12 via a person (e.g., the patient or someone else), a computer, or both. For example, the thoughts 9 of the patient 8 (e.g., the detectable neural-related signals and/or extractable features associated with the thoughts 9) can assigned the input commands 18 by the patient 8, can be assigned by a computer algorithm (e.g., based on signal strength of the detectable neural-related signal associated with the thought 9), can be changed (e.g., reassigned) by the patient 8, can be changed by an algorithm (e.g., based on relative signal strengths of switches or the availability of new repeatable thoughts 9), or any combination thereof. The input command 18 and/or the function associated with the input command 18 can be, but need not be, irrelevant to the thought 9 associated with activating the input command 18. For example, FIGS. 1A-1C illustrate an exemplary variation of a non-specific, or universal, mode switching program (e.g., an application programming interface (API)) that third parties can plug into and which allows the thoughts 9 (e.g., the detectable neural-related signals and/or extractable features associated with the thoughts 9) to be assigned and reassigned to various input commands 18. By assigning the input command 18 a thought 9 is assigned to, or vice versa, the patient 8 can use the same thought 9 for various input commands 18 in the same or different end applications 12. Similarly, by reassigning the input command 18 a thought 9 is assigned to, or vice versa, the patient 8 can use the same thought 9 for various input commands 18 in the same or different end applications 12. For example, a thought 9 assigned to an input command 18 which causes a prosthetic hand (e.g., a first end application) to open can be assigned to a different input command 18 that causes a cursor (e.g., a second end application) to do something on a computer (e.g., any function associated with a cursor associated with a mouse or touchpad of a computer, including, for example, movement of the cursor and selection using the cursor such as left click and right click).

FIGS. 1A-1C further illustrate that the thoughts 9 of a patient 8 can be assigned to multiple end applications 12, such that the patient 8 can switch between multiple end applications 12 without having to reassign input commands 18 every time the patient 8 uses a different end application 12. For example, the thoughts 9 can be assigned to multiple end applications 12 simultaneously (e.g., to both a first end application and a second end application, where the process of assigning the thought 9 to both the first and second end applications can but need not occur simultaneously). A patient's thoughts 9 can thereby advantageously control any end application 12, including, for example, external gaming devices or various house appliances and devices (e.g., light switches, appliances, locks, thermostats, security systems, garage doors, windows, shades, including, any smart device or system, etc.). The neural interface 14 can thereby detect neural-related signals 17 (e.g., brain signals) that are task-irrelevant to the functions associated with the input commands 18 of the end applications 12, where the end applications 12 can be any electronic device or software, including devices internal and/or external to the patient's body. As another example, the neural interface 14 can thereby detect neural-related signals 17 (e.g., brain signals) that are task-relevant to the functions associated with the input commands 18 of the end applications 12, where the end applications 12 can be any electronic device or software, including devices internal and/or external to the patient's body. As yet another example, the neural interface 14 can thereby detect neural-related signals 17 (e.g., brain signals) associated with task-relevant thoughts, task-irrelevant thoughts, or both task-relevant thoughts and task-irrelevant thoughts.

Some of the thoughts 9 can be task-irrelevant thoughts (e.g., the patient 8 tries moving their hand to move a cursor to the right), some of the thoughts 9 can be task-relevant thoughts (e.g., the patient 8 tries moving a cursor when the target task is to move a cursor), some of the thoughts 9 can be both a task-irrelevant thought and a task-relevant thought, or any combination thereof. Where a thought 9 is both a task-irrelevant thought and a task-relevant thought, the thought 9 can be used as both a both a task-irrelevant thought (e.g., the patient 8 tries moving their hand to move a cursor to the right) and a task-relevant thought (e.g., the patient tries moving a cursor when the target task is to move a cursor) such that the thought 9 can be associated with multiple input commands 18, where one or multiple of those input commands 18 can be task-relevant to the thought 9 and where one or multiple of those input commands 18 can be task-irrelevant to the thought 9. As another example, all of the thoughts 9 can be task-irrelevant thoughts. The thoughts 9 that are task-irrelevant and/or the thoughts 9 used by the patient 8 as task-irrelevant thoughts (e.g., the thoughts 9 assigned to input commands 18 that are irrelevant to the thought 9) the patient 8 (e.g., BCI users) to utilize a given task-irrelevant thought (e.g., the thought 9) to independently control a variety of end-applications 12, including software and devices.

FIGS. 1A-1C illustrate, for example, that the patient 8 can think about the thought 9 (e.g., with or without being asked to think about the thought 9) and then rest. This task of thinking about the thought 9 can generate a detectable neural-related signal that corresponds to the thought 9 that the patient was thinking. The task of thinking about the thought 9 and then resting can be performed once, for example, when the patient 8 thinks of the thought 9 to control the end application 12. As another example, the task of thinking about the thought 9 can be repeated multiple times, for example, when the patient 8 is controlling an end application 12 by thinking of the thought 9 or when the patient is training how use the thought 9 to control an end application 12. When a neural-related signal (e.g., brain-related signal) is recorded, such as a neural signal, features can be extracted from (e.g., spectra power/time-frequency domain) or identified in the signal itself (e.g., time-domain signal). These features can contain characteristic information about the thought 9 and can be used to identify the thought 9, to distinguish multiple thoughts 9 from one another, or to do both. As another example, these features can be used to formulate or train a mathematical model or algorithm that can predict the type of thought that generated the neural-signal using machine learning methods and other methods. Using this algorithm and/or model, what the patient 8 is thinking can be predicted in real-time and this prediction can be associated into any input command 18 desired. The process of the patient 8 thinking about the same thought 9 can be repeated, for example, until the prediction provided by the algorithm and/or model matches the thought 9 of the patient 8. In this way, the patient 8 can have each of their thoughts 9 that they will use to control an end application 12 calibrated such that each thought 9 assigned to an input command 18 generates a repeatable neural-related signal detectable by the neural interface 14. The algorithm can provide feedback 19 to the patient 8 of whether the prediction matches the actual thought 9 that they are supposed to be thinking, where the feedback can be visual, auditory and/or tactile which can induce learning by the patient 8 through trial and error. The feedback 19 can also be feedback in the form of neural stimulation. Machine learning methods and mathematical algorithms can be used to classify the thoughts 9 based on the features extracted from and/or identified in the sensed neural-related signals 17. For example, a training data set can be recorded where the patient 8 rests and thinks multiple times, the processor can extract the relevant features from the sensed neural-related signals 17, and the parameters and hyperparameters of the mathematical model or algorithm being used to distinguish between rest and thinking based on this data can be optimized to predict the real-time signal. Then, the same mathematical model or algorithm that has been tuned to predict the real-time signal advantageously allows the module 10 to translate the thoughts 9 into real-time universal switches.

FIG. 1A further illustrates that that the neural interface 14 can monitor the biological medium (e.g., the brain), such as electrical signals from the tissue (e.g., neural tissue) being monitored. FIG. 1A further illustrates that the neural-related signals 17 can be brain-related signals. The brain-related signals can be, for example, electrical signals from any portion or portions of the patient's brain (e.g., motor cortex, sensory cortex). As another example, the brain-related signals can be any signal (e.g., electrical, biochemical) detectable in the skull, can be any feature or features extracted from a detected brain-related signal (e.g., via a computer processor), or both. As yet another example, the brain-related signals can be electrical signals, can be any signal (e.g., biochemical signal) caused by an electrical signal, can be any feature or features extracted from a detected brain-related signal (e.g., via a computer processor), or any combination thereof.

FIG. 1A further illustrates that the end applications 12 can be separate from but in wired or wireless communication with the module 10. As another example, the module 10 (e.g., the host device 16) can be permanently or removably attached to or attachable to an end application 12. For example, the host device 16 can be removably docked with an application 12 (e.g., a device having software that the module 10 can communicate with). The host device 16 can have a port engageable with the application 12, or vice versa. The port can be a charging port, a data port, or both. For example, where the host device is a smartphone, the port can be a lightening port. As yet another example, the host device 16 can have a tethered connection with the application 12, for example, with a cable. The cable can be a power cable, a data transfer cable, or both.

FIG. 1B further illustrates that when the patient 8 thinks of a thought 9, the neural-related signal 17 can be a brain-related signal corresponding to the thought 9. FIG. 1B further illustrates that the host device 16 can have a processor (e.g., microprocessor) that analyzes (e.g., detects, decodes, classifies, or any combination thereof) the neural-related signals 17 received from the neural interface 14, associates the neural-related signals 17 received from the neural interface 14 to their corresponding input command 18, associates features extracted from (e.g., spectra power/time-frequency domain) or identified in the neural-related signal 17 itself (e.g., time-domain signal) received from the neural interface 14 to their corresponding input command 18, saves the neural-related signals 17 received from the neural interface 14, saves the signal analysis (e.g., the features extracted from or identified in the neural-related signal 17), saves the association of the neural-related signal 17 to the input command 18, saves the association of the features extracted from or identified in the neural-related signal 17 to the input command 18, or any combination thereof.

FIG. 1B further illustrates that the host device 16 can have a memory. The data saved by the processor can be stored in the memory locally, can be stored on a server (e.g., on the cloud), or both. The thoughts 9 and the data resulting therefrom (e.g., the detected neural-related signals 17, the extracted features, or both) can function as a reference library. For example, once a thought 9 is calibrated, the neural-related signal 17 associated with the calibrated thought and/or its signature (also referred to as extracted) features can be saved. A thought 9 can be considered calibrated, for example, when the neural-related signal 17 and/or the features extracted therefrom have a repeatable signature or feature identifiable by the processor when the neural-related signal 17 is detected by the neural interface 14. The neural-related signals being monitored and detected in real-time can then be compared to this stored calibrated data in real-time. Whenever one of the detected signals 17 and/or its extracted features match a calibrated signal, the corresponding input command 18 associated with the calibrated signal can be sent to the corresponding end application 12. For example, FIGS. 1A and 1B illustrate that the patient 8 can be trained to use the module 10 by calibrating the neural-related signals 17 associated with their thoughts 9 and storing those calibrations in a reference library. The training can provide feedback 19 to the patient 8.

FIG. 1C further illustrates an exemplary user interface 20 of the host device 16. The user interface 20 can be a computer screen (e.g., a touchscreen, a non-touchscreen). FIG. 1C illustrates an exemplary display of the user interface 20, including selectable systems 13, selectable input commands 18, and selectable end applications 12. A system 13 can be a grouping of one or multiple end applications 12. Systems 13 can be added to and removed from the host device 16. End applications 12 can be added to and removed from the host device 16. End applications 12 can be added to and removed from the systems 13. Each system 13 can have a corresponding set of input commands 18 that can be assigned to a corresponding set of end applications 12. As another example, the user interface 20 can show the input commands 18 for each of the activated end applications 12 (e.g., the remote). As yet another example, the user interface 20 can show the input commands 18 for the activated end applications (e.g., the remote) and/or for the deactivated end applications 12 (e.g., the stim sleeve, phone, smart home device, wheelchair). This advantageously allows the module 10 to control any end application 12. The user interface 20 allows the thoughts 9 to be easily assigned to various input commands 18 of multiple end applications 12. The system groupings of end applications (e.g., system 1 and system 2) advantageously allow the patient 8 to organize the end applications 12 together using the user interface 20. Ready-made systems 13 can be uploaded to the module and/or the patient 8 can create their own systems 13. For example, a first system can have all the end applications 12 the patient 8 uses that are associated with mobility (e.g., wheelchair, wheelchair lift). As another example, a second system can have all the end applications 12 the patient 8 uses that are associated with prosthetic limbs. As yet another example, a third system can have all the end applications 12 the patient 8 uses that are associated with smart household appliances. As still yet another example, a fourth system can have all the end applications 12 the patient 8 uses that are associated with software or devices that the patient uses for their occupation. End applications 12 can be in one or multiple systems 13. For example, an end application 12 (e.g., wheelchair) can be in both system 1 and/or system 2. Such organizational efficiency can make it easy for the patient 8 to manage their end applications 12. The module 10 can have one or multiple systems 13, for example, 1 to 1000 or more systems 13, including every 1 system 13 increment within this range (e.g., 1 systems, 2 systems, 10 systems, 100 systems, 500 systems, 1000 systems, 1005 systems, 2000 systems). For example, FIG. 1C illustrates that the module 10 can have a first system 13a (e.g., system 1) and a second system 13b (e.g., system 2). Also, while FIG. 1C illustrates that end applications 12 can be grouped into various systems 13, where each system has one or multiple end applications 12, as another example, the user interface 20 may not group the end applications into systems 13.

FIG. 1C further illustrates that the host device 16 can be used to assign thoughts 9 to the input commands 18. For example, a thought 9, the neural-related signal 17 associated with the thought 9, the extracted features of the neural-related signal 17 associated with the thought 9, or any combination thereof can be assigned to an input command 18 of a system 13, for example, by selecting the input command 18 (e.g., the left arrow) and selecting from a drop down menu showing the thoughts 9 and/or data associated therewith (e.g., the neural-related signal 17 associated with the thought 9, the extracted features of the neural-related signal 17 associated with the thought 9, or both) that can be assigned to the input command 18 selected. FIG. 1C further illustrates that when an input command 18 is triggered by a thought 9 or data associated therewith, feedback (e.g., visual, auditory, haptic, and/or neural stimulation feedback) can be provided to the patient 8. FIG. 1C further illustrates that the one or multiple end applications 12 can be activated and deactivated in a system 13. Activated end applications 12 may be in a powered on, a powered off, or in a standby state. Activated end applications 12 can receive triggered input commands 18. Deactivated end applications 12 may be in a powered on, a powered off, or in a standby state. In one example, deactivated end applications 12 may not be controllable by the thoughts 9 of the patient 8 unless the end application 12 is activated. Activating an end application 12 using the user interface 20 can power on the end application 12. Deactivating an end application 12 using the user interface 20 can power off the deactivated end application 12 or otherwise delink the module 10 from the deactivated end application 12 so that the processor does not associate neural-related signals 17 with the thoughts 9 assigned to the deactivated end application 12. For example, FIG. 1C illustrates an exemplary system 1 having five end applications 12, where the five end applications include 5 devices (e.g., remote, stim sleeve, phone, smart home device, wheelchair), where one of them (e.g., the remote) is activated and the others are deactivated. Once "start" is selected (e.g., via icon 20a), the patient 8 can control the end applications 12 of the systems (e.g., system 1) that are activated (e.g., the remote) with the input commands 18 associated with the end applications 12 of system 1. FIG. 1C further illustrates that any changes made using the user interface 20 can be saved using the save icon 20b and that any changes made using the user interface 20 can be canceled using the cancel icon 20c. FIG. 1C further illustrates that the end applications 12 can be electronic devices.

FIGS. 1A-1C illustrate that the same specific set of thoughts 9 can be used to control multiple end applications 12 (e.g., multiple end devices), thereby making the module 10 a universal switch module. The module 10 advantageously allows the patient 8 (e.g., BCI users) to utilize a given task-irrelevant thought (e.g., the thought 9) to independently control a variety of end-applications 12, including, for example, multiple software and devices. The module 10 can acquire neural-related signals (e.g., via the neural interface 14), can decode the acquired neural-related signals (e.g., via the processor), can associate the acquired neural-related signals 17 and/or the features extracted from these signals with the corresponding input command 18 of one or multiple end applications 12 (e.g., via the processor), and can control multiple end applications 12 (e.g., via the module 10). Using the module 10, the thoughts 9 can advantageously be used to control multiple end applications 12. For example, the module 10 can be used to control multiple end applications 12, where a single end application 12 can be controlled at a time. As another example, the module 10 can be used to control multiple end applications simultaneously. Each thought 9 can be assigned to an input command 18 of multiple applications 12. In this way, the thoughts 9 can function as universal digital switches, where the module 10 can effectively reorganize the patient's motor cortex to represent digital switches, where each thought 9 can be a digital switch. These digital switches can be universal switches, usable by the patient 8 to control multiple end applications 12, as each switch is assignable (e.g., via the module 10) to any input command 18 of multiple end applications 12 (e.g., an input command of a first end application and an input command of a second end application). The module 10 can, via the processor, discern between different thoughts 9 (e.g., between different switches).

The module 10 can interface with, for example, 1 to 1000 or more end applications 12, including every 1 end application 12 increment within this range (e.g., 1 end application, 2 end applications, 10 end applications, 100 end applications, 500 end applications, 1000 end applications, 1005 end applications, 2000 end applications). For example, FIG. 1C illustrates that the first system 13a can have a first end application 12a (e.g., a remote), a second end application 12b (e.g., a stim sleeve), a third end application 12c (e.g., a phone), a fourth end application 12d (e.g., a smart home device), and a fifth end application 12e (e.g., a wheelchair).

Each end application can have, for example, 1 to 1000 or more input commands 18 that can be associated with the thoughts 9 of the patient 8, or as another example, 1 to 500 or more input commands 18 that can be associated with the thoughts 9 of the patient 8, or as yet another example, 1 to 100 or more input commands 18 that can be associated with the thoughts 9 of the patient 8, including every 1 input command 18 within these ranges (e.g., 1 input command, 2 input commands, 10 input commands, 100 input commands, 500 input commands, 1000 input commands, 1005 input commands, 2000 input commands), and including any subrange within these ranges (e.g., 1 to 25 or less input commands 18, 1 to 100 or less input commands 18, 25 to 1000 or less input commands 18) such that any number of input commands 18 can be triggered by the patient's thoughts 9, where any number can be, for example, the number of input commands 18 that the thoughts 9 of the patient 8 are assigned to. For example, FIG. 1C illustrates an exemplary set of input commands 18 that are associated with the activated end application(s) 12 (e.g., the first end application 12a), including a first end application first input command 18a (e.g., left arrow), a first end application second input command 18b (e.g., right arrow), and a first end application third input command 18c (e.g., enter). As another example, FIG. 1C illustrates an exemplary set of input commands 18 that are associated with the deactivated end application(s) 12 (e.g., the second end application 12b), including a second end application first input command 18d (e.g., choose an output), where the second end application first input command 18d has not been selected yet, but can be any input command 18 of the second end application 12b. The first end application first input command 18a is also referred to as the first input command 18a of the first end application 12a. The first end application second input command 18b is also referred to as the second input command 18b of the first end application 12a. The first end application third input command 18c is also referred to as the third input command 18c of the first end application 12a. The second end application first input command 18d is also referred to as the first input command 18d of the second end application 12b.

When the patient 8 thinks of a thought 9, the module 10 (e.g., via the processor) can associate the neural-related signals 17 associated with the thought 9 and/or features extracted therefrom with the input commands 18 that the thought 9 is assigned to, and the input commands 18 associated with the thought 9 can be sent to their corresponding end applications 12 by the module 10 (e.g., via a processor, a controller, or a transceiver). For example, if the thought 9 is assigned to the first input command 18a of the first end application 18a, the first input command 18a of the first end application 12a can be sent to the first end application 12a when the patient 8 thinks of the thought 9, and if the thought 9 is assigned to the first input command 18d of the second end application 12b, the first input command 18d of the second end application 12b can be sent to the second end application 12b when the patient 8 thinks of the thought 9. A single thought (e.g., the thought 9) can thereby interface with, or be used to control, multiple end applications 12 (first and second end applications 12*a*, 12*b*). Any number of thoughts 9 can be used as switches. The number of thoughts 9 used as switches can correspond to, for example, the number of controls (e.g., input commands 18) needed or desired to control an end application 12. A thought 9 can be assignable to multiple end applications 12. For example, the neural-related signals 17 and/or the features extracted therefrom that are associated with a first thought can be assigned to the first end application first input command 18*a* and can be assigned to the second end application first input command 18*d*. As another example, the neural-related signals 17 and/or the features extracted therefrom that are associated with a second thought can be assigned to the first end application second input command 18*a* and can be assigned to a third end application first input command. The first thought can be different from the second thought. The multiple end applications 12 (e.g., the first and second end applications 12*a*, 12*b*) can be operated independently from one another. Where the module 10 is used to control a single end application (e.g., the first end application 12*a*), a first thought can be assignable to multiple input commands 18. For example, the first thought alone can activate a first input command, and the first thought together with the second thought can activate a second input command different from the first input command. The thoughts 9 can thereby function as a universal switch even where only a single end application 12 is being controlled by the module 10, as a single thought can be combinable with other thoughts to make additional switches. As another example, a single thought can be combinable with other thoughts to make additional universal switches that are assignable to any input command 18 where multiple end applications 12 are controllable by the module 10 via the thoughts 9.

FIGS. 2A-2D illustrate that the neural interface 14 can be a stent 101. The stent 101 can have struts 108 and sensors 131 (e.g., electrodes). The stent 101 can be collapsible and expandable.

FIGS. 2A-2D further illustrate that the stent 101 can be implanted in the vasculature of the subject, for example, a vessel traversing a sinus or vein of the subject. As a more specific example, the stent 101 can be implanted within a superior sagittal sinus of the subject. FIG. 2A illustrates an exemplary module 10 and FIGS. 2B-2D illustrate three magnified views of the module 10 of FIG. 2A. The stent 101 can be implanted for example, via the jugular vein, into the superior sagittal sinus (SSS) overlying the primary motor cortex to passively record brain signals and/or stimulate tissue. The stent 101, via the sensors 131, can detect neural-related signals 17 that are associated with the thought 9, for example, so that people who are paralyzed due to neurological injury or disease, can communicate, improve mobility and potentially achieve independent through direct brain control of assistive technologies such as end applications 12. FIG. 2C illustrates that the communication conduit 24 (e.g., the stent lead) can extend from the stent 101, pass through a wall of the jugular, and tunnel under the skin to a subclavian pocket. In this way, the communication conduit 24 can facilitate communications between the stent 101 and the telemetry unit 22.

FIGS. 2A-2D further illustrate that the end application 12 can be a wheelchair.

Figure 3:
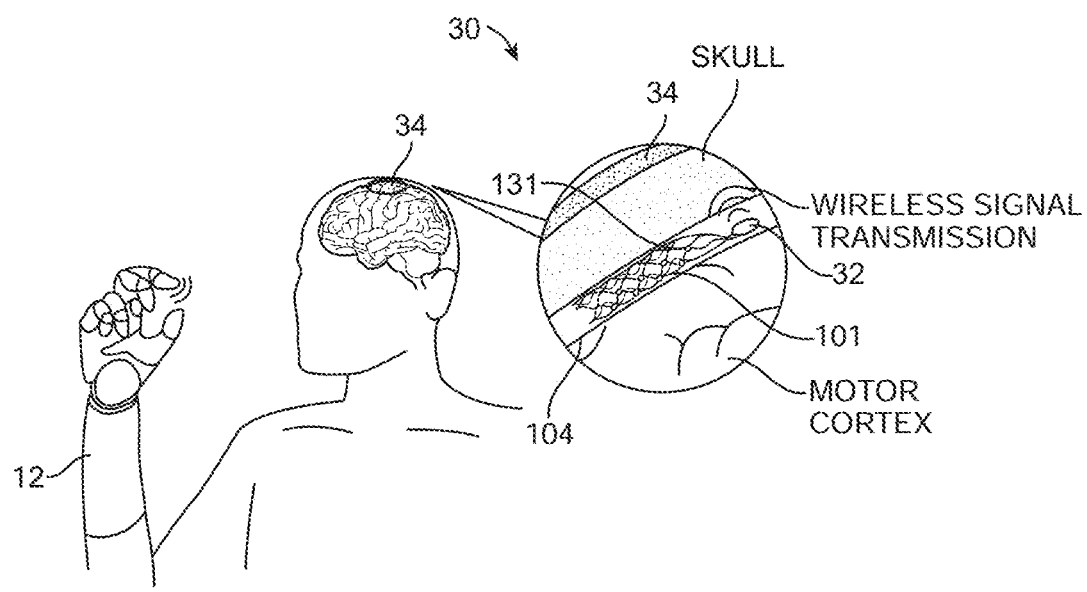
FIG. 3 illustrates a variation of a wireless universal switch module in communication with an end application.

FIG. 3 illustrates that the neural interface 14 (e.g., stent 101) can be a wireless sensor system 30 that can wirelessly communicate with the host device 16 (e.g., without the telemetry unit 22). FIG. 3 illustrates the stent 101 within a blood vessel 104 overlying the motor cortex in the patient 8 that are picking up neural-related signals and relaying this information to a wireless transmitter 32 located on the stent 101. The neural-related signals recorded by the stent 101 can be wirelessly transmitted through the patient's skull to a wireless transceiver 34 (e.g., placed on the head), which in turn, decodes and transmits the acquired neural-related signals to the host device 16. As another example, the wireless transceiver 34 can be part of the host device 16.

FIG. 3 further illustrates that the end application 12 can be a prosthetic arm.

Figure 4:
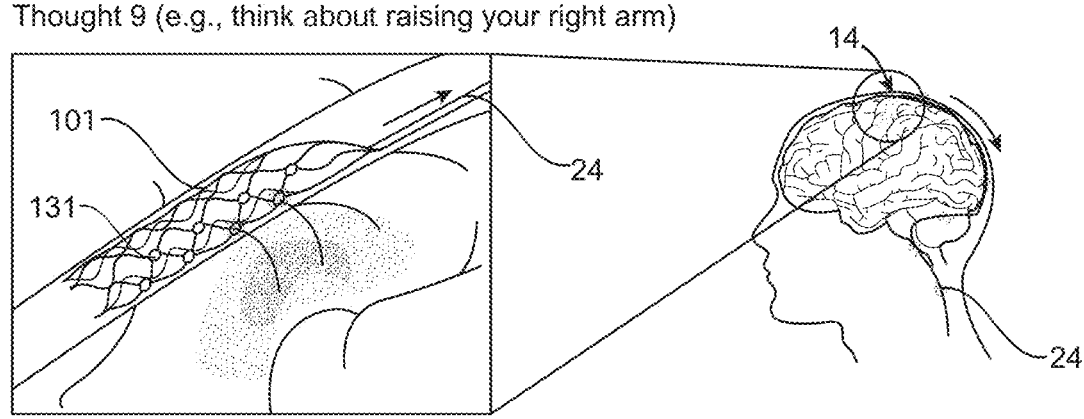
FIG. 4 illustrates a variation of a universal switch module being used to record neural-related signals of a patient.

FIG. 4 illustrates that the neural interface 14 (e.g., the stent 101) can be used to record neural-related signals 17 from the brain, for example, from neurons in the superior sagittal sinus (SSS) or branching cortical veins, including the steps of: (a) implanting the neural interface 14 in a vessel 104 in the brain (e.g., the superior sagittal sinus, the branching cortical veins); (b) recording neural-related signals; (c) generating data representing the recorded neural-related signals; and (d) transmitting the data to the host device 16 (e.g., with or without the telemetry unit 22).

Everything in U.S. Pat. No. 10,512,555 is herein incorporated by reference in its entirety for all purposes, including all systems, devices, and methods disclosed therein, and including any combination of features and operations disclosed therein. For example, the neural interface 14 (e.g., the stent 101) can be, for example, any of the stents (e.g., stents 101) disclosed in U.S. Pat. No. 10,512,555.

Moreover, the neural interface, stents, or scaffolds disclosed herein can be any of the stents, scaffolds, stent-electrodes, or stent-electrode arrays disclosed in U.S. Patent Pub. No. US 2020/0363869; U.S. Patent Pub. No. 2020/0078195; U.S. Patent Pub. No. 2020/0016396; U.S. Patent Pub. No. 2019/0336748; U.S. Patent Pub. No. US 2014/0288667; U.S. Pat. Nos. 10,575,783; 10,485,968; 10,729,530; International Patent App. No. PCT/US2020/059509 filed on Nov. 6, 2020; U.S. patent application Ser. No. 62/927,574 filed on Oct. 29, 2019; U.S. patent application Ser. No. 62/932,906 filed on Nov. 8, 2019; U.S. patent application Ser. No. 62/932,935 filed on Nov. 8, 2019; U.S. patent application Ser. No. 62/935,901 filed on Nov. 15, 2019; U.S. patent application Ser. No. 62/941,317 filed on Nov. 27, 2019; U.S. patent application Ser. No. 62/950,629 filed on Dec. 19, 2019; U.S. patent application Ser. No. 63/003,480 filed on Apr. 1, 2020; U.S. patent application Ser. No. 63/057,379 filed on Jul. 28, 2020, and U.S. patent application Ser. No. 63/062,633 filed on Aug. 7, 2020, the contents of which are incorporated herein by reference in their entireties.

Using the module 10, the patient 8 can be prepared to interface with multiple end applications 12. Using the module 10, the patient 8 can perform multiple tasks with the use of one type of electronic command which is a function of a particular task-irrelevant thought (e.g., the thought 9). For example, using the module 10, the patient 8 can perform multiple tasks with a single task-irrelevant thought (e.g., the thought 9).

Figure 5:
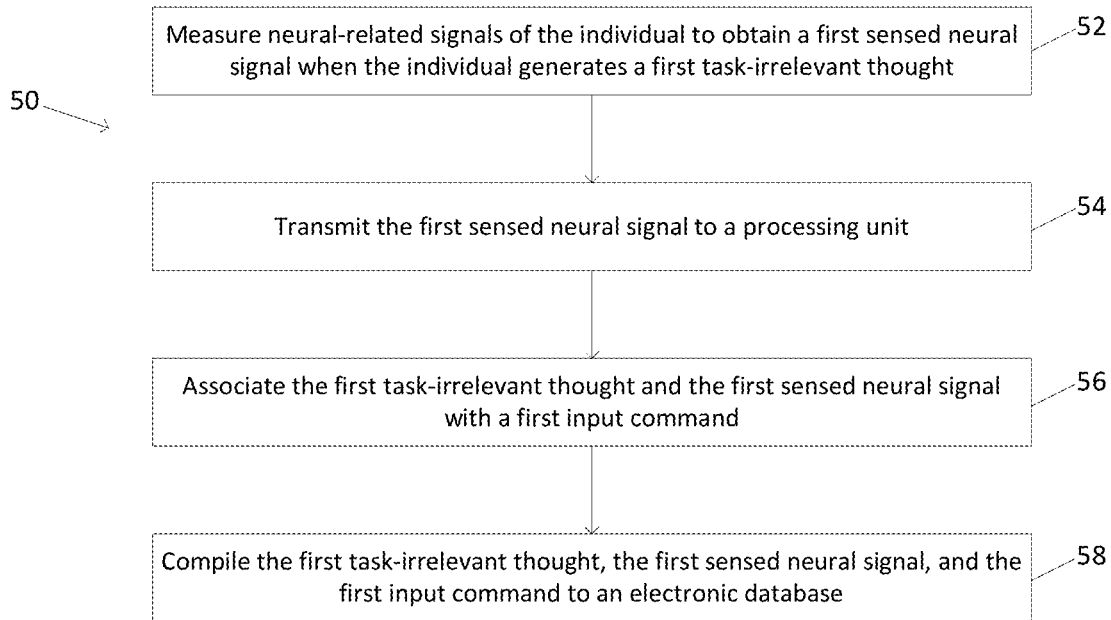
FIG. 5 illustrates a variation of a method undertaken by the universal switch module of FIGS. 1A-1C.

For example, FIG. 5 illustrates a variation of a method 50 of preparing an individual to interface with an electronic device or software (e.g., with end applications 12) having operations 52, 54, 56, and 58. FIG. 5 illustrates that the method 50 can involve measuring neural-related signals of the individual to obtain a first sensed neural signal when the individual generates a first task-irrelevant thought in operation 52. The method 50 can involve transmitting the first sensed neural signal to a processing unit in operation 54. The method 50 can involve associating the first task-irrelevant thought and the first sensed neural signal with a first input command in operation 56. The method 50 can involve compiling the first task-irrelevant thought, the first sensed neural signal, and the first input command to an electronic database in operation 58.

Figure 6:
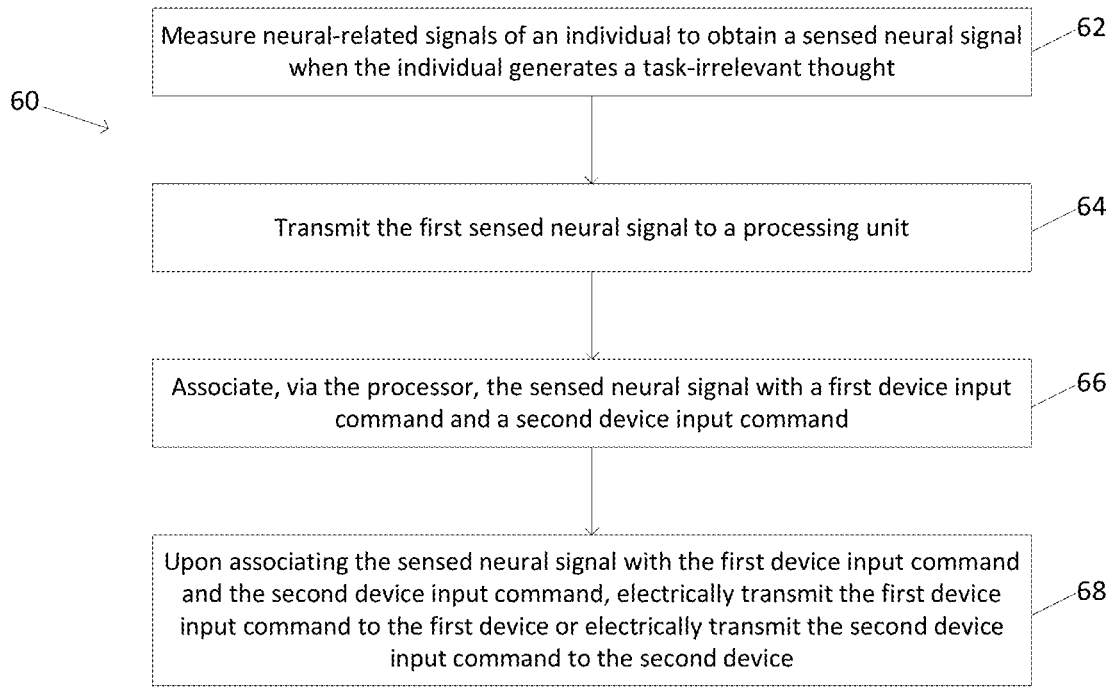
FIG. 6 illustrates a variation of a method undertaken by the universal switch module of FIGS. 1A-1C.

As another example, FIG. 6 illustrates a variation of a method 60 of controlling a first device and a second device (e.g., first and second end applications 12a, 12b) having operations 62, 64, 66, and 68. FIG. 6 illustrates that the method 60 can involve measuring neural-related signals of an individual to obtain a sensed neural signal when the individual generates a task-irrelevant thought in operation 62. The method 60 can involve transmitting the sensed neural signal to a processor in operation 64. The method can involve associating, via the processor, the sensed neural signal with a first device input command and a second device input command in operation 66. The method can involve upon associating the sensed neural signal with the first device input command and the second device input command, electrically transmitting the first device input command to the first device or electrically transmitting the second device input command to the second device in operation 68.

Figure 7:
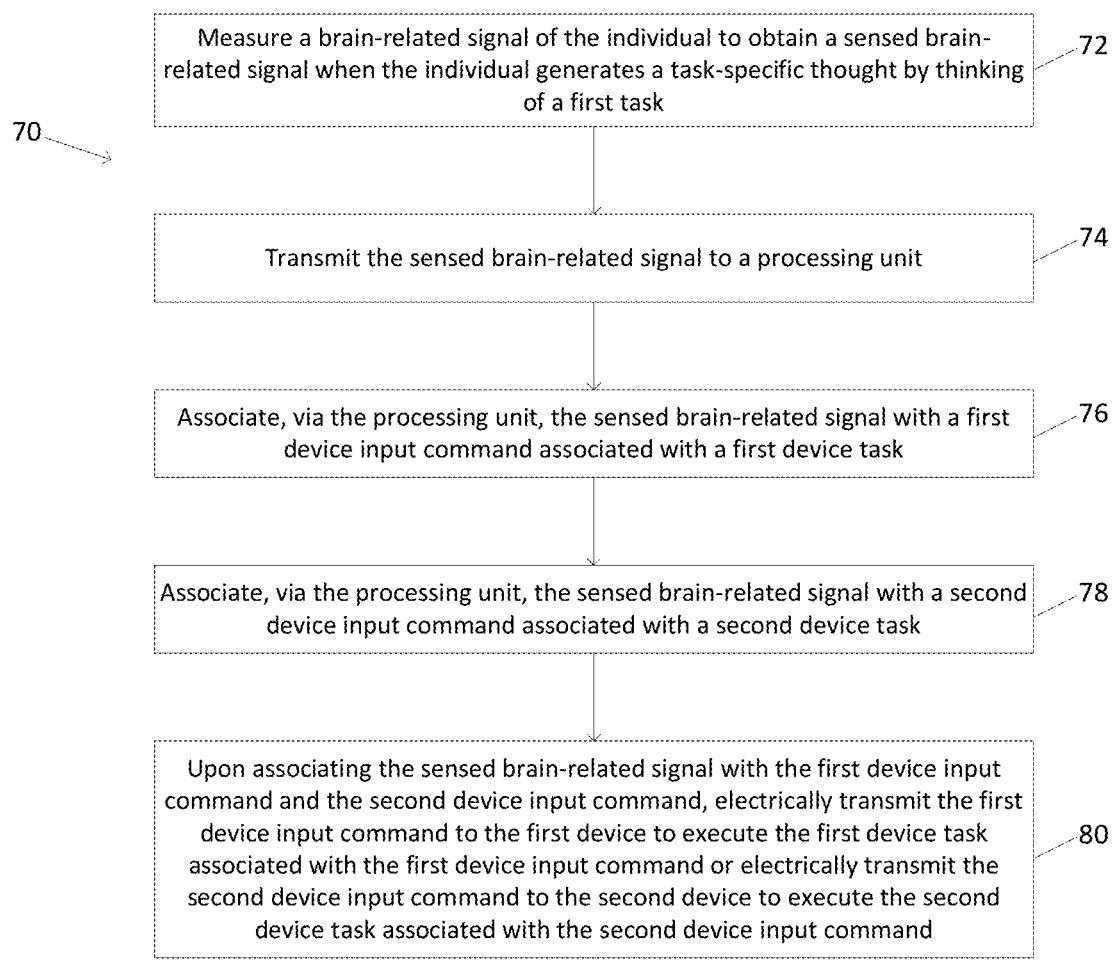
FIG. 7 illustrates a variation of a method undertaken by the universal switch module of FIGS. 1A-1C.

As another example, FIG. 7 illustrates a variation of a method 70 of preparing an individual to interface with a first device and a second device (e.g., first and second end applications 12a, 12b) having operations 72, 74, 76, 78, and 80. FIG. 7 illustrates that the method 70 can involve measuring a brain-related signal of the individual to obtain a sensed brain-related signal when the individual generates a task-specific thought by thinking of a first task in operation 72. The method can involve transmitting the sensed brain-related signal to a processing unit in operation 74. The method can involve associating, via the processing unit, the sensed brain-related signal with a first device input command associated with a first device task in operation 76. The first device task can be different from the first task. The method can involve associating, via the processing unit, the sensed brain-related signal with a second device input command associated with a second device task in operation 78. The second device task can be different from the first device task and the first task. The method can involve upon associating the sensed brain-related signal with the first device input command and the second device input command, electrically transmitting the first device input command to the first device to execute the first device task associated with the first device input command or electrically transmitting the second device input command to the second device to execute the second device task associated with the second device input command in operation 80.

As another example, FIGS. 5-7 illustrate variations of methods of controlling multiple end applications 12 with a universal switch (e.g., the thought 9).

As another example, the operations illustrated in FIGS. 5-7 can be executed and repeated in any order and in any combination. FIGS. 5-7 do not limit the present disclosure in any way to the methods illustrated or to the particular order of operations that are listed. For example, the operations listed in methods 50, 60, and 70 can be performed in any order or one or more operations can be omitted or added.

As another example, a variation of a method using the module 10 can include measuring brain-related signals of the individual to obtain a first sensed brain-related signal when the individual generates a task-irrelevant thought (e.g., the thought 9). The method can include transmitting the first sensed brain-related signal to a processing unit. The method can include the processing unit applying a mathematical algorithm or model to detect the brain-related signals corresponding to when the individual generates the thought 9.

The method can include associating the task-irrelevant thought and the first sensed brain-related signal with one or multiple N input commands 18. The method can include compiling the task-irrelevant thought (e.g., the thought 9), the first sensed brain-related signal, and the N input commands 18 to an electronic database. The method can include monitoring the individual for the first sensed brain-related signal (e.g., using the neural interface), and upon detecting the first sensed brain-related signal electrically transmitting at least one of the N input commands 18 to a control system. The control system can be a control system of an end application 12. The N input commands 18 can be, for example, 1 to 100 input commands 18, including every 1 input command 18 within this range. The N input commands can be assignable to Y end applications 12, where the Y end applications can be, for example, 1 to 100 end applications 12, including every 1 end application 12 increment within this range. As another example, the Y end applications 12 can be, for example, 2 to 100 end applications 12, including every 1 end application 12 increment within this range. The Y end applications 12 can include, for example, at least one of controlling a mouse cursor, controlling a wheelchair, and controlling a speller. The N input commands 18 can be at least one of a binary input associated with the task-irrelevant thought, a graded input associated with the task-irrelevant thought, and a continuous trajectory input associated with the task-irrelevant thought. The method can include associating M detections of the first sensed brain-related signal with the N input commands 18, where M is 1 to 10 or less detections. For example, when M is one detection, the task-irrelevant thought (e.g., the thought 9) and the first sensed brain-related signal can be associated with a first input command (e.g., first input command 18a). As another example, when M is two detections, the task-irrelevant thought (e.g., the thought 9) and the first sensed brain-related signal can be associated with a second input command (e.g., first input command 18b). As yet another example, when M is three detections, the task-irrelevant thought (e.g., the thought 9) and the first sensed brain-related signal can be associated with a third input command (e.g., third input command 18c). The first, second, and third input commands can be associated with one or multiple end applications 12. For example, the first input command can be an input command for a first end application, the second input command can be an input command for a second end application, and the third input command can be an input command for a third application, such that a single thought 9 can control multiple end applications 12. Each number of M detections of the thought 9 can be assigned to multiple end applications, such that end number of M detections (e.g., 1, 2, or 3 detections) can function as a universal switch assignable to any input command 18. The first, second, and third input commands can be associated with different functions. The first, second, and third input commands can be associated with the same function such that the first input command is associated with a function first parameter, such that the second input command is associated with a function second parameter, and such that the third input command is associated with a function third parameter. The function first, second, and third parameters can be, for example, progressive levels of speed, volume, or both. The progressive levels of speed can be, for example, associated with movement of a wheelchair, with movement of a mouse cursor on a screen, or both. The progressive levels of volume can be, for example, associated with sound volume of a sound system of a car, a computer, a telephone, or any combination thereof. At least one of the N input commands

18 can be a click and hold command associated with a computer mouse. The method can include associating combinations of task-irrelevant thoughts (e.g., the thoughts 9) with the N input commands 18. The method can include associating combinations of Z task-irrelevant thoughts with the N input commands 18, where the Z task-irrelevant thoughts can be 2 to 10 or more task-irrelevant thoughts, or more broadly, 1 to 1000 or more task-irrelevant thoughts, including every 1 unit increment within these ranges. At least one of the Z task-irrelevant thoughts can be the task-irrelevant thought, where the task-irrelevant thought can be a first task-irrelevant thought, such that the method can include measuring brain-related signals of the individual to obtain a second sensed brain-related signal when the individual generates a second task-irrelevant thought, transmitting the second sensed brain-related signal to a processing unit, associating the second task-irrelevant thought and the second sensed brain-related signal with N2 input commands, where when a combination of the first and second sensed brain-related signals are sequentially or simultaneously obtained, the combination can be associated with N3 input commands. The task-irrelevant thought can be the thought of moving a body limb. The first sensed brain-related signal can be at least one of an electrical activity of brain tissue and a functional activity of the brain tissue. Any operation in this exemplary method can be performed in any combination and in any order.

As another example, a variation of a method using the module 10 can include measuring a brain-related signal of the individual to obtain a first sensed brain-related signal when the individual generates a first task-specific thought by thinking of a first task (e.g., by thinking of the thought 9). The method can include transmitting the first sensed brain-related signal to a processing unit. The method can include the processing unit applying a mathematical algorithm or model to detect the brain-related signals corresponding to when the individual generates the thought. The method can include associating the first sensed brain-related signal with a first task-specific input command associated with a second task (e.g., an input command 18), where the second task is different from the first task (e.g., such that the thought 9 involves a different task than the task that the input command 18 is configured to execute). The first task-specific thought can be irrelevant to the associating step. The method can include assigning the second task to the first task-specific command instruction irrespective of the first task. The method can include reassigning a third task to the first task-specific command instruction irrespective of the first task and the second task. The method can include compiling the first task-specific thought, the first sensed brain-related signal, and the first task-specific input command to an electronic database. The method can include monitoring the individual for the first sensed brain-related signal, and upon detecting the first sensed brain-related signal electrically transmitting the first task-specific input command to a control system. The first task-specific thought can be, for example, about a physical task, a non-physical task, or both. The thought generated can be, for example, a single thought or a compound thought. The compound thought can be two or more non-simultaneous thoughts, two or more simultaneous thoughts, and/or a series of two or more simultaneous thoughts. Any operation in this exemplary method can be performed in any combination and in any order.

As another example, a variation of a method using the module 10 can include measuring a brain-related signal of the individual to obtain a first sensed brain-related signal when the individual thinks a first thought. The method can include transmitting the first sensed brain-related signal to a processing unit. The method can include the processing unit applying a mathematical algorithm or model to detect the brain-related signals corresponding to when the individual generates the thought. The method can include generating a first command signal based on the first sensed brain-related signal. The method can include assigning a first task to the first command signal irrespective of the first thought. The method can include disassociating the first thought from the first sensed electrical brain activity. The method can include reassigning a second task to the first command signal irrespective of the first thought and the first task. The method can include compiling the first thought, the first sensed brain-related signal, and the first command signal to an electronic database. The method can include monitoring the individual for the first sensed brain-related signal, and upon detecting the first sensed brain-related signal electrically transmitting the first input command to a control system. The first thought can involve, for example, a thought about a real or imagined muscle contraction, a real or imagined memory, or both, or any abstract thoughts. The first thought can be, for example, a single thought or a compound thought. Any operation in this exemplary method can be performed in any combination and in any order.

As another example, a variation of a method using the module 10 can include measuring electrical activity of brain tissue of the individual to obtain a first sensed electrical brain activity when the individual thinks a first thought. The method can include transmitting the first sensed electrical brain activity to a processing unit. The method can include the processing unit applying a mathematical algorithm or model to detect the brain-related signals corresponding to when the individual generates the thought. The method can include generating a first command signal based on the first sensed electrical brain activity. The method can include assigning a first task and a second task to the first command signal. The first task can be associated with a first device, and where the second task is associated with a second device. The first task can be associated with a first application of a first device, and where the second task is associated with a second application of the first device. The method can include assigning the first task to the first command signal irrespective of the first thought. The method can include assigning the second task to the first command signal irrespective of the first thought. The method can include compiling the first thought, the first sensed electrical brain activity, and the first command signal to an electronic database. The method can include monitoring the individual for the first sensed electrical brain activity, and upon detecting the first sensed electrical brain activity electrically transmitting the first command signal to a control system. Any operation in this exemplary method can be performed in any combination and in any order.

As another example, a variation of a method using the module 10 can include measuring neural-related signals of the individual to obtain a first sensed neural signal when the individual generates a task-irrelevant thought. The method can include transmitting the first sensed neural signal to a processing unit. The method can include the processing unit applying a mathematical algorithm or model to detect the brain-related signals corresponding to when the individual generates the task-irrelevant thought. The method can include associating the task-irrelevant thought and the first sensed neural signal with a first input command. The method can include compiling the task-irrelevant thought, the first sensed neural signal, and the first input command to an electronic database. The method can include monitoring the individual for the first sensed neural signal, and upon detecting the first sensed neural signal electrically transmitting the first input command to a control system. The neural-related signals can be brain-related signals. The neural-related signals can be measured from neural tissue in the individual's brain. Any operation in this exemplary method can be performed in any combination and in any order.

As another example, a variation of a method using the module 10 can include measuring a neural-related signal of the individual to obtain a first sensed neural-related signal when the individual generates a first task-specific thought by thinking of a first task. The method can include transmitting the first sensed neural-related signal to a processing unit. The method can include the processing unit applying a mathematical algorithm or model to detect the brain-related signals corresponding to when the individual generates the thought. The method can include associating the first sensed neural-related signal with a first task-specific input command associated with a second task, where the second task is different from the first task, thereby providing a mechanism to the user to control multiple tasks with different task-specific inputs with a single user-generated thought The method can include compiling the task-irrelevant thought, the first sensed neural signal, the first input command and the corresponding tasks to an electronic database. The method can include utilizing the memory of the electronic database to automatically group the combination of task-irrelevant thought, sensed brain-related signal and one or multiple N input based on the task, brain-related signal or the thought to automatically map the control functions for automatic system setup for use. The neural-related signal can be a neural-related signal of brain tissue. Any operation in this exemplary method can be performed in any combination and in any order.

The module 10 can perform any combination of any method and can perform any operation of any method disclosed herein.

Figure 8:
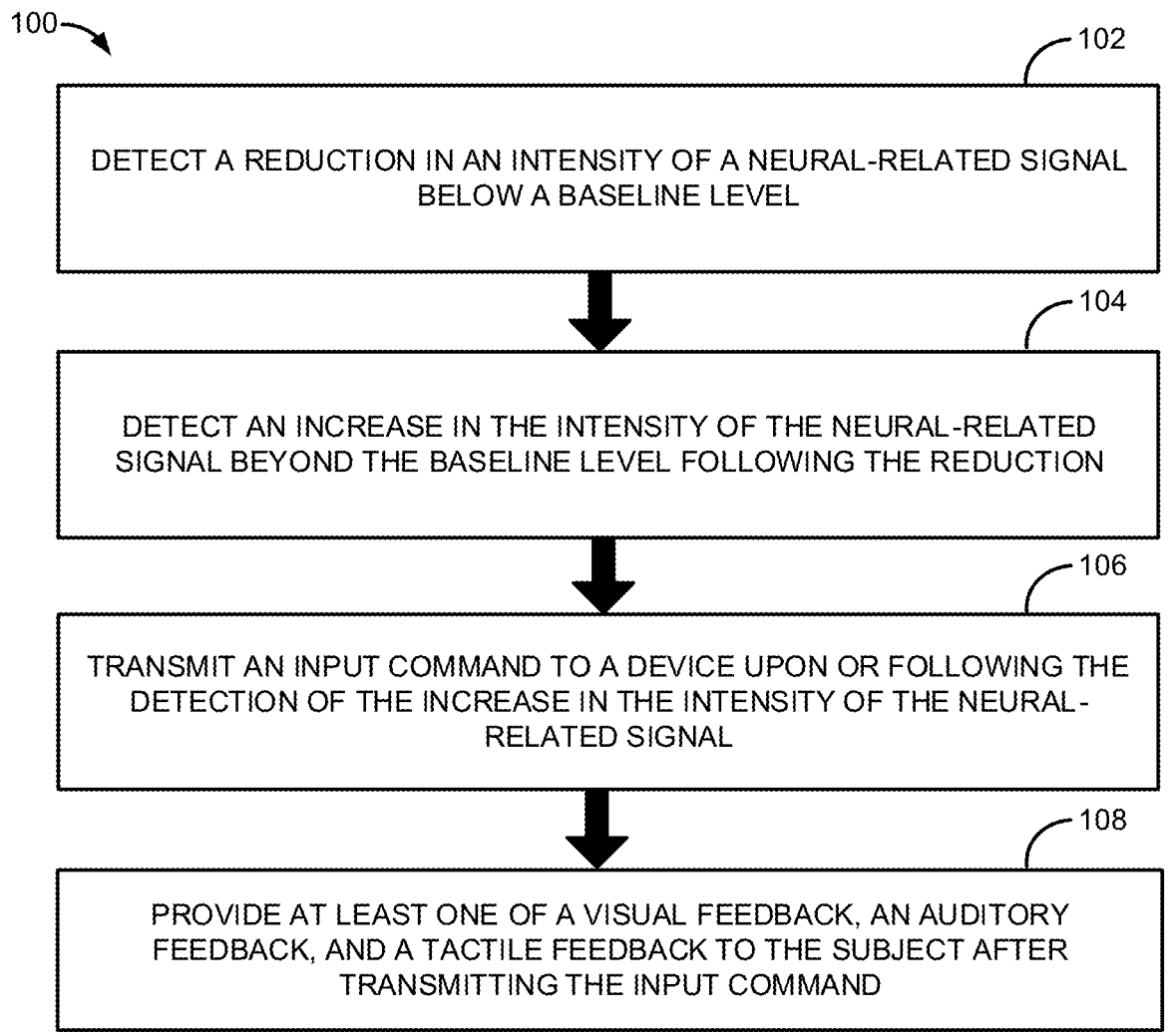
FIG. 8 illustrates a variation of a method for controlling a device or software using detected changes in a neural-related signal of a subject.

FIG. 8 illustrates an embodiment of a method 100 for controlling a device (e.g., a personal electronic device, an IoT device, a mobility vehicle, etc.), a software application (e.g., an end application 12), or a combination thereof using detected changes in a neural-related signal of a subject. In some embodiments, the neural-related signal can be brainwaves or other types of synchronized electrical brain activity of the subject.

The neural-related signal can comprise one or more neural oscillations of the subject including neural oscillations in a beta frequency range or beta-band (about 12 Hz to 30 Hz), an alpha frequency range or alpha-band (about 7 Hz to 12 Hz), a gamma frequency range or gamma-band (about 30 Hz to 140 Hz, more specifically, 60 Hz to 80 Hz), a delta frequency range or delta-band (about 0.1 Hz to 3 Hz), a theta frequency range or theta-band (about 4 Hz to 7 Hz), or a combination thereof. The neural-related signal can also comprise neural oscillations in the Mu band (about 7.5 Hz to 12.5 Hz), sensorimotor rhythm (SMR) band (about 12.5 Hz to 15.5 Hz), or a combination thereof.

As described in the preceding sections, the neural-related signal of the subject can be monitored or measured using the module 10 or components thereof, For example, the neural-related signal can be monitored or measured using the neural interface 14, telemetry unit 22, the host device 16, or a combination thereof.

In some embodiments, the neural interface 14 can be an endovascular device (e.g., an expandable and collapsible stent) implanted within the subject. In certain embodiments, the neural-related signal can be monitored or measured using electrodes of the neural interface 14 implanted within the subject. For example, the neural-related signal can be monitored or measured using electrodes of the implantable endovascular device (e.g., electrodes coupled to the stent).

As previously discussed, the endovascular device can be implanted within the brain of the subject. For example, the endovascular device can be implanted within at least one of a frontal cortex, a motor cortex, and a sensory cortex of the subject. The endovascular device can also be implanted in other parts of the brain of the subject.

The method 100 can comprise detecting a reduction in an intensity of a neural-related signal of the subject below a baseline level in operation 102. For example, detecting the reduction in the intensity of the neural-related signal can comprise detecting a reduction in the power (e.g., measured in micro-volts squared per Hz ($\mu V^2/Hz$), decibels (dBs), average t-scores, average z-scores, etc.) of at least one neural oscillation of the subject (e.g., a neural oscillation at a beta-band frequency).

In some embodiments, the baseline level can be defined as a mean intensity or average intensity over a certain time period (e.g., over the last few seconds or minutes). In these and other embodiments, the baseline level can vary or be continuously adjusted and set. In other embodiments, the baseline level can be a predefined or predetermined level. For example, the baseline level can be determined based on a time-of-day, an activity or action undertaken by the subject, or a combination thereof.

The reduction in the intensity of the neural-related signal can refer to a statistically significant (e.g., more than 2 standard deviations (SDs)) reduction in the intensity of the neural-related signal relative to the baseline level. This statistically significant reduction in the intensity of the neural-related signal can also be referred to as a desynchronization or desynch of the neural-related signal.

For example, when the neural-related signal monitored or measured is a beta-band oscillation, the method 100 can comprise detecting a statistically significant drop or reduction in the power of the beta-band oscillation relative to a baseline beta-band power level. More specifically, this statistically significant decrease in the power of the beta-band oscillation can be referred to as a beta-desynchronization.

The method 100 can also comprise detecting a subsequent increase in the intensity of the neural-related signal beyond the baseline level following the reduction in operation 104. For example, the method 100 can comprise detecting a statistically significant (e.g., more than 2 SDs) increase in the intensity of the neural-related signal beyond the baseline level. In some embodiments, this statistically significant increase in the intensity of the neural-related signal can be referred to as a rebound of the neural-related signal.

For example, when the neural-related signal monitored or measured is a beta-band oscillation, the method 100 can comprise detecting a statistically significant increase or rise in the power of the beta-band oscillation relative to a baseline beta-band power level. More specifically, this statistically significant increase in the power of the beta-band oscillation can be referred to as a beta-rebound.

In certain embodiments, the power of a select number of neural frequency bands (e.g., beta-band, gamma-band, etc.) can be monitored continuously across selected channels using electrodes coupled to the neural interface 14 and the power readings can be filtered and fed into a machine-learning classifier at predetermined intervals (e.g., every 100 milliseconds or 100 ms). The machine learning classifier can then classify the power into a discrete state or event such as a (1) desynchronization ("desynch") event, a (2) rebound event, or a (3) rest or non-event by comparing the power against a baseline level for that particular neural frequency band.

The intensity change can be detected using the neural interface 14 (e.g., via electrodes of the endovascular device implanted within the brain) and one or more processors of the telemetry unit 22, the host device 16, or a combination thereof.

The method 100 can further comprise transmitting an input command 18 to the device or software upon or following the detection of the increase in the intensity of the neural-related signal in operation 106. In some embodiments, the input command 18 can be transmitted upon or following the detection of the increase in the intensity of the neural-related signal but before a completion of the signal rebound.

The input command 18 can be transmitted using one or more processors of the telemetry unit 22, the host device 16, or a combination thereof. As previously discussed, the input command 18 can be transmitted to one or more end applications (e.g., application software) run on a peripheral or personal computing device such as a laptop, a desktop computer, a smartphone, or a tablet computer. When the input command 18 is transmitted to a software program, the input command 18 can be transmitted via one or more software application programming interfaces (APIs). In these and other embodiments, the input command 18 can be transmitted to an IoT device, a mobility vehicle (such as an electric wheelchair), or other types of peripheral or personal computing devices to control such devices or vehicles. Moreover, the input command 18 can also be transmitted to one or more end applications (e.g., software) run on such peripheral or personal computing devices or vehicles.

In some embodiments, the reduction in the intensity of the neural-related signal can be caused by the subject conjuring or generating a task-relevant thought and holding the task-relevant thought for a period of time. In these embodiments, the subsequent increase in the intensity of the neural-related signal (e.g., the signal rebound) can be caused by the subject mentally releasing the task-relevant thought. Also, in these embodiments, the input command 18 can be a command transmitted to a device or software to accomplish at least part of a task associated with the task-relevant thought.

For example, a method of controlling an electric wheelchair can comprise a subject generating and holding a thought to move the electric wheelchair forward. The module 10 can detect a reduction in the intensity of a neural-related signal of the subject (e.g., a beta-oscillation desynchronization) as the subject holds the thought of moving the electric wheelchair forward. The module 10 can then detect a subsequent increase in the intensity of the subject's neural-relate signal (e.g., a beta-oscillation rebound) as the subject releases the thought of moving the electric wheelchair forward. The module 10 can then transmit an input command 18 to the electric wheelchair to move the electric wheelchair forward upon detecting the increase in the intensity of the subject's neural-relate signal. As can be appreciated by one of ordinary skill in the art, this method can be expanded to cover any number of task-relevant thoughts and to cover control of other devices, vehicles, or software not specifically mentioned in the preceding example.

In other embodiments, the reduction in the intensity of the neural-related signal can be caused by the subject conjuring or generating a task-irrelevant thought and holding the task-relevant thought for a period of time. In these embodiments, the subsequent increase in the intensity of the neural-related signal can be caused by the subject mentally releasing the task-irrelevant thought. Also, in these embodiments, the input command 18 can be a command transmitted to a device or software to accomplish at least part of a task not associated with the task-irrelevant thought.

For example, another method of controlling an electric wheelchair can comprise a subject generating and holding a thought related to a body function of the subject such as contracting a muscle of the subject. The thought related to the body function of the subject can be considered a task-irrelevant thought since it does not relate to the task of controlling the subject's electric wheelchair. The module 10 can detect a reduction in the intensity of a neural-related signal of the subject (e.g., a beta-oscillation desynchronization) as the subject holds the thought of contracting the muscle of the subject. The module 10 can then detect a subsequent increase in the intensity of the subject's neural-relate signal (e.g., a beta-oscillation rebound) as the subject releases the thought of contracting the muscle of the subject. The module 10 can then transmit an input command 18 to the electric wheelchair to move the electric wheelchair forward upon detecting the increase in the intensity of the subject's neural-relate signal. As can be appreciated by one of ordinary skill in the art, this method can be expanded to cover any number of task-irrelevant thoughts and to cover control of other devices, vehicles, or software not specifically mentioned in the preceding example.

The method 100 can also comprise an additional operation 108 of providing a visual feedback, an auditory feedback, a tactile feedback, feedback in the form of neural stimulation, or a combination thereof to the subject after transmitting the input command 18 to the device or software. The feedback can inform the subject that the input command 18 has been successfully transmitted or that the input command 18 is in the process of being implemented. In other embodiments, the feedback can inform the subject that a signal desynchronization or a signal rebound has been detected.

In some embodiments, the visual feedback can comprise written text being displayed through a display of the host device 16. In other embodiments, the visual feedback can comprise one or more lights being lit on the telemetry unit 22, or the host device 16, or a combination thereof. The auditory feedback can comprise one or more sounds or auditory alerts generated by the telemetry unit 22 or the host device 16. In other embodiments, the auditory feedback can comprise a computer-generated or pre-recorded audio message being played by the telemetry unit 22 or the host device 16. The tactile feedback can comprise one or more sensors or electronic components configured to provide physically perceptible feedback to the subject in the form of vibrations, motions, or other forces applied to the subject's body or appendages. In some embodiments, the tactile feedback can be applied to the subject through the telemetry unit 22, an additional wearable unit, a seat, a structure, or a platform supporting the subject, or a combination thereof. Feedback in the form of neural stimulation can comprise transmitting electrical impulses through electrodes implanted within the subject. For example, neural stimulation feedback can comprise transmitting electrical impulses to the brain of the subject through electrodes of the neural interface 14 implanted within the brain of the subject. In other embodiments, neural stimulation feedback can comprise non-invasive stimulation such as stimulation of the subject via transcranial direct current stimulation (tDCS), transcranial magnetic stimulation (TMS), transcranial alternating current stimulation (tACS), transcranial pulsed current stimulation (tPCS), transcranial random noise stimulation (tRNS), or a combination thereof.

Figure 9:
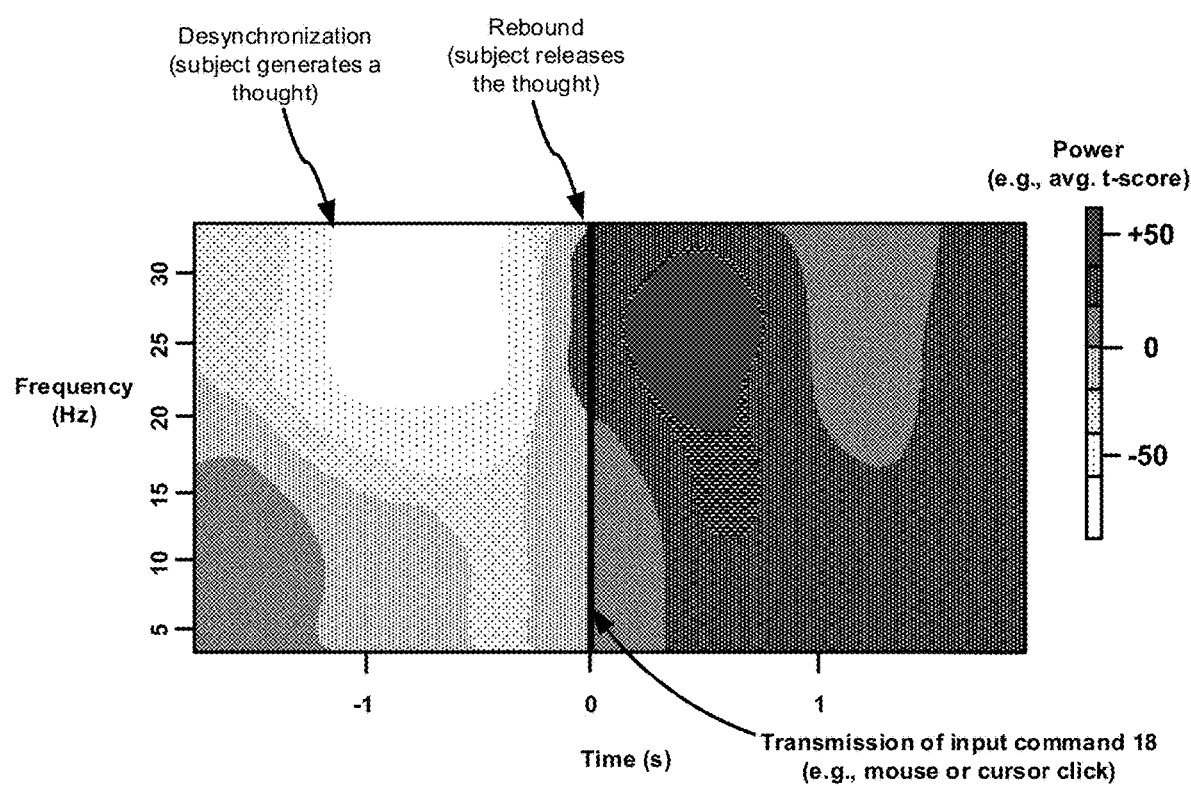
FIG. 9 illustrates an example spectrogram illustrating a detected change in a neural-related signal of a subject.

FIG. 9 illustrates a spectrogram showing a desynchronization (or reduction) of a neural oscillation of the subject in the beta-band or beta-frequency followed by a rebound (or increase) of the beta-band neural oscillation. More specifically, the spectrogram shows a reduction in the power of the beta-band oscillation below a baseline power level followed by an increase in the power beyond the baseline power level. In this particular spectrogram, the power is expressed as average t-scores. The power can also be expressed as decibels (dB), z-scores, or $\mu V^2/Hz$.

The desynchronization of the neural-related signal can be caused by the subject conjuring or generating a thought (such as a task-relevant thought or task-irrelevant thought) and holding the thought for a period of time. The rebound of the neural-related signal can be caused by the subject mentally releasing the thought.

FIG. 9 also illustrates that the input command 18 can be transmitted following or upon the detection of the signal rebound. The input command 18 is transmitted before the completion of the signal rebound. As will be discussed in more detail in the following sections, the duration of the desynchronization can play a role in determining which input command(s) 18 to transmit to the device or software program.

Figure 10:
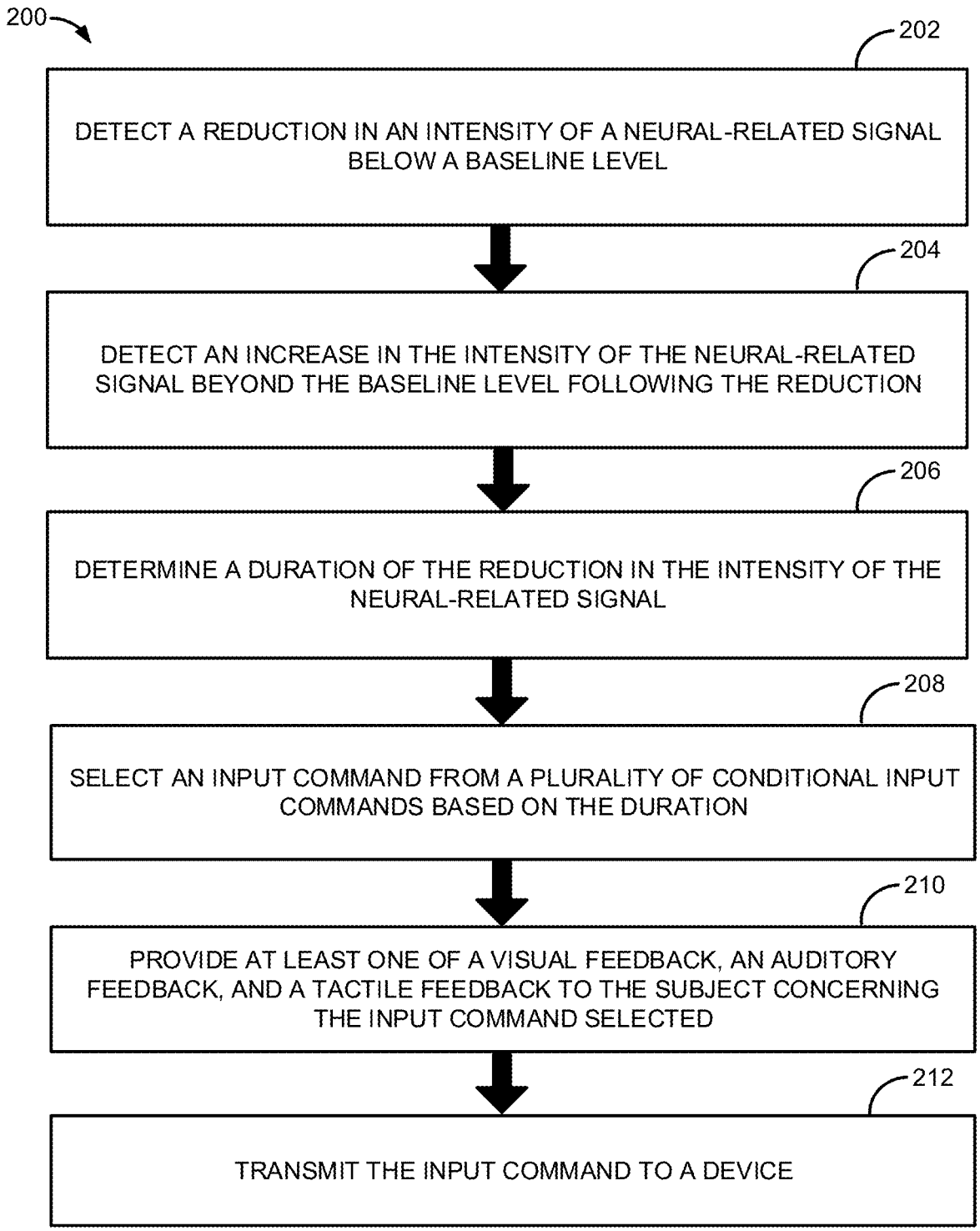
FIG. 10 illustrates another variation of a method for controlling a device or software using detected changes in a neural-related signal of a subject.

FIG. 10 illustrates another method 200 for controlling a device (e.g., a personal electronic device, an IoT device, a mobility vehicle, etc.) or software program (e.g., an end application 12) using detected changes in a neural-related signal of a subject. The method 200 can comprise detecting a reduction in the intensity of a neural-related signal of the subject below a baseline level in operation 202. For example, detecting the reduction in the intensity of the neural-related signal can comprise detecting a reduction in the power of at least one neural oscillation of the subject.

The baseline level can be defined as a mean intensity or average intensity over a certain time period. The baseline level can vary or be continuously adjusted and set. In other embodiments, the baseline level can be a predefined or predetermined level. The reduction in the intensity of the neural-related signal can refer to a statistically significant reduction in the intensity of the neural-related signal relative to the baseline level. In some embodiments, this statistically significant decrease in the power of the beta-band oscillation can be referred to as a desynchronization or desynch of the neural-related signal.

The method 200 can also comprise detecting an increase in the intensity of the neural-related signal beyond the baseline level following the reduction in operation 204. For example, the method 100 can comprise detecting a statistically significant increase in the intensity of the neural-related signal beyond the baseline level. In some embodiments, the increase in the intensity of the neural-related signal can be referred to as a rebound of the neural-related signal.

Similar to the preceding section, the neural-related signals can be brainwaves or other types of synchronized electrical brain activity of the subject. The neural-related signal can comprise one or more neural oscillations of the subject including neural oscillations in the beta frequency range or beta-band, the alpha frequency range or alpha-band, the gamma frequency range or gamma-band, the delta frequency range or delta-band, the theta frequency range or theta-band, or a combination thereof. The neural-related signal can also comprise neural oscillations in the Mu band, the SMR band, or a combination thereof.

The neural-related signal of the subject can be monitored or measured using the module 10 or components thereof, For example, the neural-related signal can be monitored or measured using the neural interface 14, telemetry unit 22, the host device 16, or a combination thereof.

The neural interface 14 can be an endovascular device (e.g., an expandable and collapsible stent) implanted within the brain of the subject. In certain embodiments, the neural-related signal can be monitored or measured using electrodes of the neural interface 14 implanted within the brain of the subject. For example, the neural-related signal can be monitored or measured using electrodes of a stent implanted within the brain of the subject.

The method 200 can further comprise determining a duration of the reduction in the intensity of the neural-related signal in operation 206. For example, when the neural-related signal is a beta-band oscillation, operation 206 can comprise determining the duration of the desynchronization of the beta-band oscillation.

As will be discussed in more detail in the following sections, in some embodiments, the power of a select number of neural frequency bands (e.g., beta-band, gamma-band, etc.) can be monitored continuously across selected channels using electrodes coupled to the neural interface 14 and the power readings can be filtered and fed into a machine-learning classifier at predetermined intervals (e.g., every 100 milliseconds). The machine learning classifier can then classify the power into a discrete state or event such as a (1) desynchronization ("desynch") event, a (2) rebound event, or a (3) rest or non-event by comparing the power against a baseline level for that particular neural frequency band. In these embodiments, determining the duration of a signal desynchronization can comprise counting the number of consecutive desynchronization events preceding a rebound event.

In other embodiments, determining the duration of the reduction in the intensity of the neural-related signal can comprise transmitting a first signal to the telemetry unit 22, the host device 16, or another device serving as part of the module 10 when the reduction in the intensity of the neural-related signal is first detected and transmitting a second signal to the telemetry unit 22, the host device 16, or the other device serving as part of the module 10 when the reduction in the intensity of the neural-related signal ceases or a signal rebound is detected. The telemetry unit 22, the host device 165, or the other device serving as part of the module 10 can then determine the duration by calculating an elapsed time between the two signals.

The method 200 can also comprise selecting an input command 18 from a plurality of conditional input commands based on the duration in operation 208. Selecting the input command 18 from the plurality of conditional input commands can further comprise comparing the duration with one or more temporal thresholds associated with the conditional input commands and selecting the input command 18 based on whether the duration exceeds or fails to reach the one or more temporal thresholds.

For example, two conditional input commands can be associated with the following temporal thresholds:

COMMAND 1: 300 ms≤duration<1000 ms (i.e., between 3 to 9 consecutive desynch events)

COMMAND 2: 1000 ms≤duration (i.e., 10 or more consecutive desynch events)

The temporal thresholds can range between 100 ms to 30,000 ms (or 30 seconds). Although a range is provided, it is contemplated by this disclosure and it should be understood by one of ordinary skill in the art that any subrange of the range disclosed is also acceptable. For example, a range of 100 ms to 30,000 ms can include 100 ms to 500 ms, 100 ms to 1000 ms, 100 ms to 10,000 ms, 1000 ms to 10,000 ms, or any other subrange within the range. In alternative embodiments, the temporal thresholds can range between 100 ms to greater than 30,000 ms such as 50,000 ms, 60,000 ms, 100,000 ms, etc.

Furthermore, the plurality of conditional input commands can comprise between two conditional input commands to ten or more conditional input commands. Each conditional input command can be associated with one or more temporal thresholds. For example, in some cases where there are two conditional input commands, the two conditional input commands can be associated with the same temporal threshold. In this example, the input command can be selected based on whether the duration reaches/exceeds the temporal threshold or fails to reach the temporal threshold.

As another example, three conditional input commands can be associated with the following temporal thresholds:

COMMAND 1 (e.g., open software application #1): 100 ms≤duration<1000 ms

COMMAND 2 (e.g., open software application #2): 1000 ms≤duration<2000 ms

COMMAND 3 (e.g., open software application #3): 2000 ms≤duration

In some embodiments, the reduction in the intensity of the neural-related signal can be caused by the subject conjuring and holding a thought (e.g., a task-relevant thought or a task-irrelevant thought). Moreover, the increase in the intensity of the neural-related signal can be caused by the same subject mentally releasing the thought. The duration of the reduction in the intensity of the neural-related signal can then be tied to the amount of time the thought (e.g., the task-relevant thought or the task-irrelevant thought) is held by the subject before the subject mentally releases the thought.

As previously discussed, the thought can be a task-relevant thought or a task-irrelevant thought. The subject can conjure and hold a task-relevant thought in order to transmit the input command 18 to a device to accomplish at least part of a task associated with the task-relevant thought. In some embodiments, the length of time the subject holds the task-relevant thought can dictate which input command is selected from a plurality of conditional input commands but all such conditional input commands can be aimed at accomplishing at least part of the task associated with the task-relevant thought.

The subject can also conjure and hold a task-irrelevant thought in order to transmit an input command to a device to accomplish at least part of a task not associated with the task-irrelevant thought. In some embodiments, the length of time the subject holds the task-irrelevant thought can dictate which input command is selected from a plurality of conditional input commands but all such conditional input commands can be aimed at accomplishing at least part of a task not associated with the task-irrelevant thought.

The method 200 can also comprise an additional or optional operation 210 of providing a visual feedback, an auditory feedback, a tactile feedback, feedback in the form of neural stimulation, or a combination thereof to the subject concerning the input command 18 selected. The feedback can inform that subject of the input command 18 selected and also provide the subject an option to correct the input command 18 by selecting a different input command 18 or cancel the input command 18 selected.

The method 200 can also comprise transmitting the input command 18 selected to the device or software in operation 212. The input command 18 can be transmitted upon or following the subject confirming the input command 18 selected or the input command 18 can be transmitted without receiving such confirmation.

The input command 18 can be transmitted using one or more processors of the telemetry unit 22, the host device 16, or a combination thereof. As previously discussed, the input command 18 can be transmitted to one or more end applications (e.g., application software) run on a peripheral or personal computing device such as a laptop, a desktop computer, a smartphone, or a tablet computer. When the input command 18 is transmitted to a software program, the input command 18 can be transmitted via one or more software application programming interfaces (APIs). In these and other embodiments, the input command 18 can be transmitted to an IoT device, a mobility vehicle (such as an electric wheelchair), or other types of peripheral or personal computing devices to control such devices or vehicles. Moreover, the input command 18 can also be transmitted to one or more end applications (e.g., software) run on such peripheral or personal computing devices or vehicles.

The method 200, or a variation thereof, can be used by the subject to control the subject's electric wheelchair when the subject generates and holds a thought to move the electric wheelchair forward for about 2 seconds. The module 10 can detect a reduction in the intensity of a neural-related signal of the subject lasting about 2 seconds. The module 10 can then detect a subsequent increase in the intensity of the subject's neural-relate signal (e.g., a beta-oscillation rebound) as the subject releases the thought of moving the electric wheelchair forward. The module 10 can then select an input command 18 from a plurality of conditional input commands based on the duration of about 2 seconds. In this case, the input command 18 can be a command to the electric wheelchair to move the electric wheelchair forward two meters. The other conditional input commands can comprise commands to move the electric wheelchair forward one meter (a desynch duration of 1 second or less) or three meters (a desynch duration of three seconds or more). The module 10 can then transmit the input command 18 to the electric wheelchair to move the electric wheelchair forward two meters. As can be appreciated by one of ordinary skill in the art, this method can be expanded to cover any number of task-relevant thoughts and to cover control of other devices, vehicles, or software not specifically mentioned in the preceding example.

The method 200, or a variation thereof, can also be used by the subject to control the subject's electric wheelchair when the subject generates and holds a thought related to a body function of the subject (e.g., contracting a muscle of the subject) for about 2 seconds. The thought related to the body function of the subject can be considered a task-irrelevant thought since it does not relate to the task of controlling the subject's electric wheelchair. The module 10 can detect a reduction in the intensity of a neural-related signal of the subject lasting about 2 seconds. The module 10 can then select an input command 18 from a plurality of conditional input commands based on the duration of about 2 seconds. In this case, the input command 18 can be a command to the electric wheelchair to move the electric wheelchair forward two meters. The other conditional input commands can comprise commands to move the electric wheelchair forward one meter (a desynch duration of 1 second or less, e.g., caused by the subject generating and holding a thought to contract a muscle for 1 second or less)

or three meters (a desynch duration of three seconds or more, e.g., caused by the subject generating and holding a thought to contract a muscle for 3 seconds or more). The module 10 can then transmit the input command 18 to the electric wheelchair to move the electric wheelchair forward two meters.

As can be appreciated by one of ordinary skill in the art, this method can be expanded to cover any number of task-irrelevant thoughts and to cover control of other devices, vehicles, or software not specifically mentioned in the preceding example.

Figure 11:
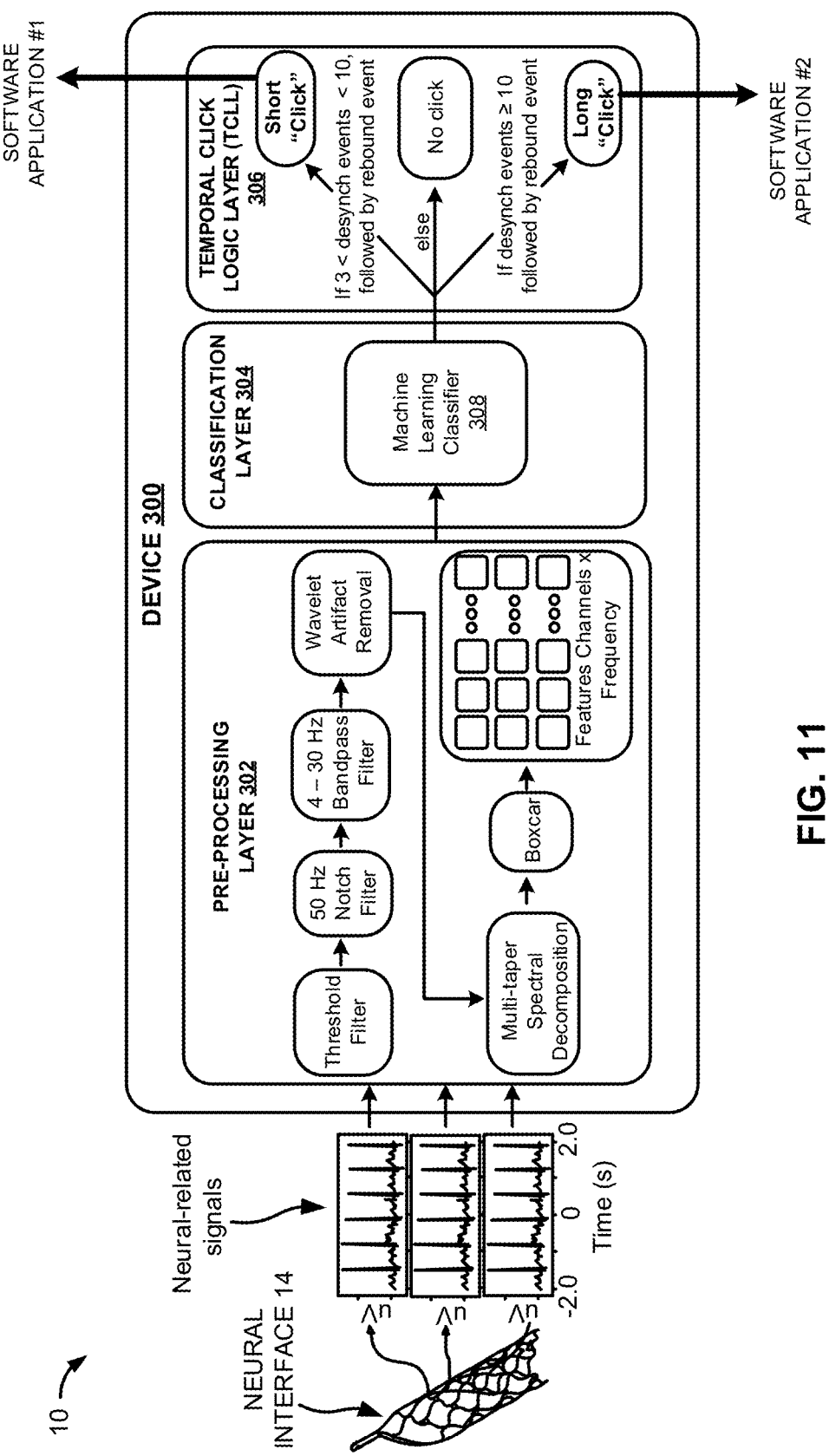
FIG. 11 illustrates another variation of a module for controlling a device or software using detected changes in a neural-related signal of a subject.

FIG. 11 illustrates a system or another embodiment of the module 10 comprising the neural interface 14 and at least one device 300 or apparatus running various software layers configured to process and classify the neural-related signals and select an input command 18 based on the processed and classified data. In some embodiments, the device 300 can be any of the telemetry unit 22, the host device 16, or a combination thereof. In these and other embodiments, the device 300 (e.g., the telemetry unit 22) can be implanted within the subject such as within a pectoral region or arm of the subject.

In other embodiments, the device 300 can refer to a processing unit or controller embedded within the neural interface 14 or coupled to the neural interface 14 implanted within the brain of the subject. One or more processors of the device 300 can be programmed to execute software instructions making up the various software layers.

As shown in FIG. 11, the software layers can comprise a pre-processing layer 302, a classification layer 304, and a temporal click logic layer 306. The pre-processing layer 302, the classification layer 304, and the temporal click logic layer 306 can be part of a multi-layered software architecture.

The pre-processing layer 302 can comprise a number of software filters configured to filter and smooth out the raw signals obtained from the neural interface 14. Neural-related signals of the subject can be monitored continuously across selected channels using electrodes of the neural interface 14 (e.g., a stent implanted within the brain of the subject). The neural-related signals can be sampled every 100 ms or 100 ms "chunks" or bins of the raw signals can be passed to the pre-processing layer 302 for processing and smoothing. As previously discussed, the neural-related signals monitored can be one or more neural frequency bands (e.g., beta-band oscillations, gamma-band oscillations, etc.) of the subject and the intensity of the neural-related signal can be the power of such neural frequency bands.

For example, data corresponding to 100 ms bins of raw neural-related signals obtained from three separate channels of the neural interface 14 can be passed first to the pre-processing layer 302. The pre-processing layer 302 can then apply: a (1) threshold filter to perform threshold-based disconnection and ratification rejection, a (2) notch filter to perform 50 Hz notch filtering, a (3) bandpass filter to perform 4-30 Hz Butterworth bandpass filtering, a (4) wavelet artifact removal filter to perform wavelet-based artifact rejection, a (5) multi-taper spectral decomposition filter to perform multi-taper spectral decomposition, and a (6) boxcar smoothing filter to perform temporal boxcar smoothing. The filtered data is then fed to the classification layer 304.

The classification layer 304 comprises a machine learning classifier configured to classify the resulting data segments or bins into: a desynchronization event or state (also known as a "key-down" classification event), a rebound event or state (also known as a "key-up" classification event), or a rest event or state. The machine learning classifier can be a pre-trained classifier.

In some embodiments, the machine learning classifier can utilize a supervised learning model such as a support vector machine (SVM). As a more specific example, the machine learning classifier can be a pre-trained SVM. In other embodiments, the machine learning classifier can be a Gaussian mixture model classifier, a Naive Bayes classifier, or another machine learning classifier.

The classified events or states can then be fed to the temporal click logic layer 306 to select an input command 18 based on the number of events/states and conditions or thresholds stored as part of the temporal click logic layer 306. For example, the temporal click logic layer 306 can select one input command to open a first software application (e.g., the subject's Gmail® application) when the temporal click logic layer 306 detects between three to nine consecutive desynch events followed by a rebound event. Alternatively, the temporal click logic layer 306 can select another input command to open a second software application (e.g., the subject's WhatsApp® application) when the temporal click logic layer 306 detects between ten or more consecutive desynch events followed by a rebound event.

Figure 12A:
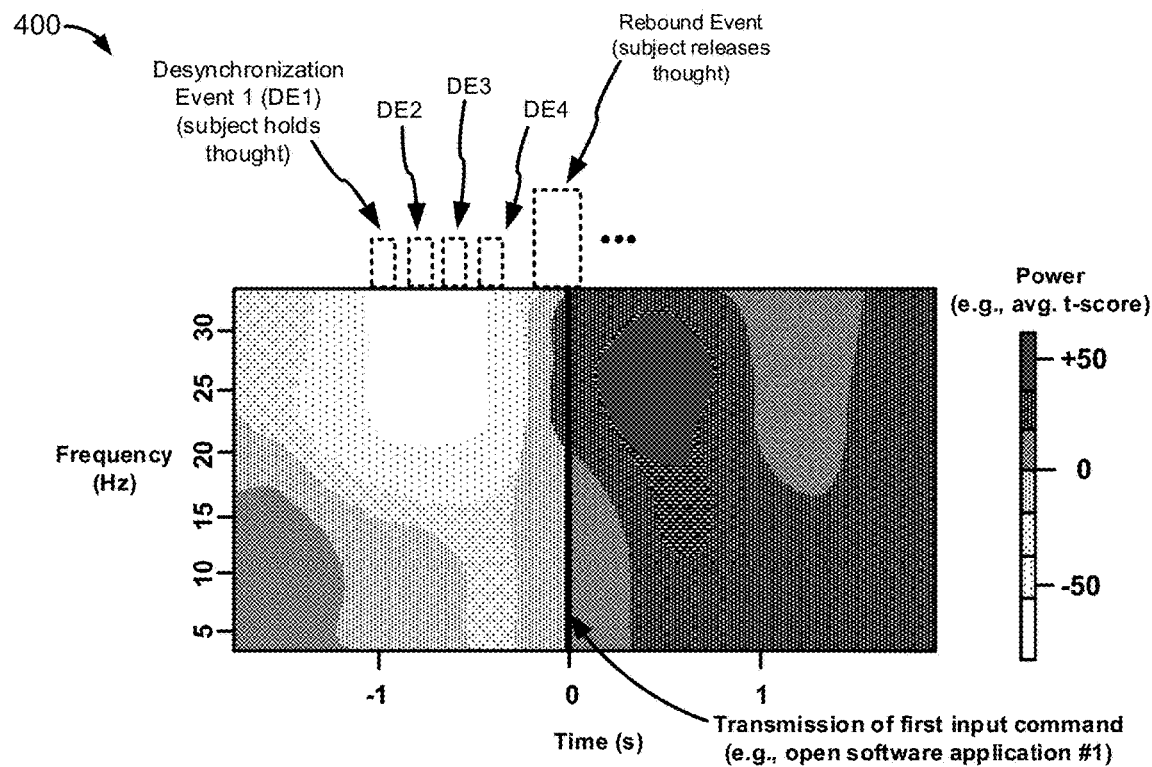
FIG. 12A illustrates an example spectrogram illustrating a subject holding a thought for a short duration.

FIG. 12A illustrates an example spectrogram 400 of a subject holding a thought for a short duration. The thought can be a task-relevant thought (e.g., pressing a mouse cursor to select a software application) or a task-irrelevant thought (e.g., contracting a hamstring of the subject). In this example, the neural-related signal can be a beta-band neural oscillation of the subject. As shown in FIG. 12A, the power of the subject's beta-band neural oscillation can decrease below a baseline beta-band power level as the subject conjures up and holds the thought.

As long as the subject holds the thought, the classification layer 304 (see FIG. 11) will classify the beta-band neural oscillation as being in a desynch state. More specifically, as long as the subject holds the thought, the classification layer 304 will classify temporal segments (e.g., 100 ms "bins") of the beta-band signal as consecutive desynch events. When a subject holds a thought for approximately 400 ms, this is roughly equivalent to four consecutive desynchronization events where each desynchronization event is set at approximately 100 ms.

FIG. 12A also illustrates that the power of the subject's beta-band neural oscillation can increase beyond a baseline beta-band power level as the subject mentally releases the thought. When this release occurs, the classification layer 304 will classify this temporal segment of the beta-band signal as a rebound event.

Once the temporal click logic layer 306 detects a rebound event, the number of consecutive desynch events preceding the rebound event will be counted and this total will be compared against one or more temporal thresholds associated with certain conditional input commands.

In this example, the four consecutive desynch events (corresponding to the subject holding the thought for approximately 400 ms) falls within a short duration range of between three consecutive desynch events (about 300 ms) and nine consecutive desynch events (about 900 ms). As a result, a first input command associated with this short duration range can be selected. The first input command can be a command to open a first software application, such as the subject's Gmail® application, run on a device in communication with the module 10. As shown in FIG. 12A, the input command can be transmitted to the device immediately after the rebound event is detected.

Figure 12B:
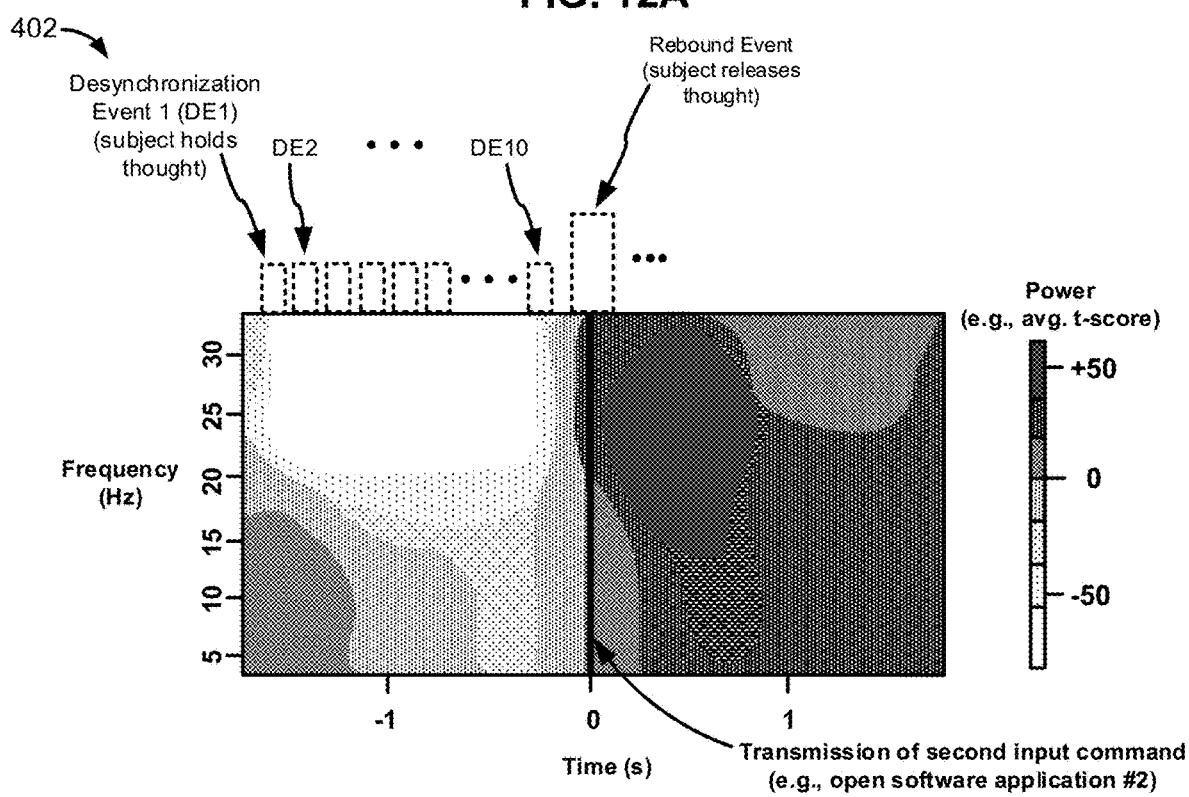
FIG. 12B illustrates an example spectrogram illustrating a subject holding a thought for a longer duration.

FIG. 12B illustrates another example spectrogram 402 of the subject holding a thought for a longer duration. As shown in FIG. 12B, the subject can hold this thought (e.g., task-relevant thought or task-irrelevant thought) for approximately 1000 ms or 1 second. Similar to FIG. 12A, the power of the subject's beta-band neural oscillation can decrease below a baseline beta-band power level as the subject conjures up and holds the thought. As seen in FIG. 12B, holding the thought for approximately 1000 ms is roughly equivalent to ten consecutive desynchronization events where each desynchronization event is set at approximately 100 ms.

The power of the subject's beta-band neural oscillation can increase beyond a baseline beta-band power level as the subject mentally releases the thought. When this release occurs, the classification layer 304 will classify this temporal segment of the beta-band signal as a rebound event.

In this example, the ten consecutive desynch events (corresponding to the subject holding the thought for approximately 1000 ms) falls within a long duration range of ten or more consecutive desynch events (x≥1000 ms). As a result, a second input command associated with this long duration range can be selected. The second input command can be a command to open a second software application, such as the subject's WhatsApp® application, run on a device in communication with the module 10. As shown in FIG. 12B, the input command can be transmitted to the device immediately after the rebound event is detected.

Although consecutive desynch events are discussed in the preceding examples, it is contemplated by this disclosure that for neural frequency bands other than beta-band frequencies, consecutive events other than desynch events (e.g., increases in the intensity of neural-related signals) can also be used to select input commands.

Figure 13:
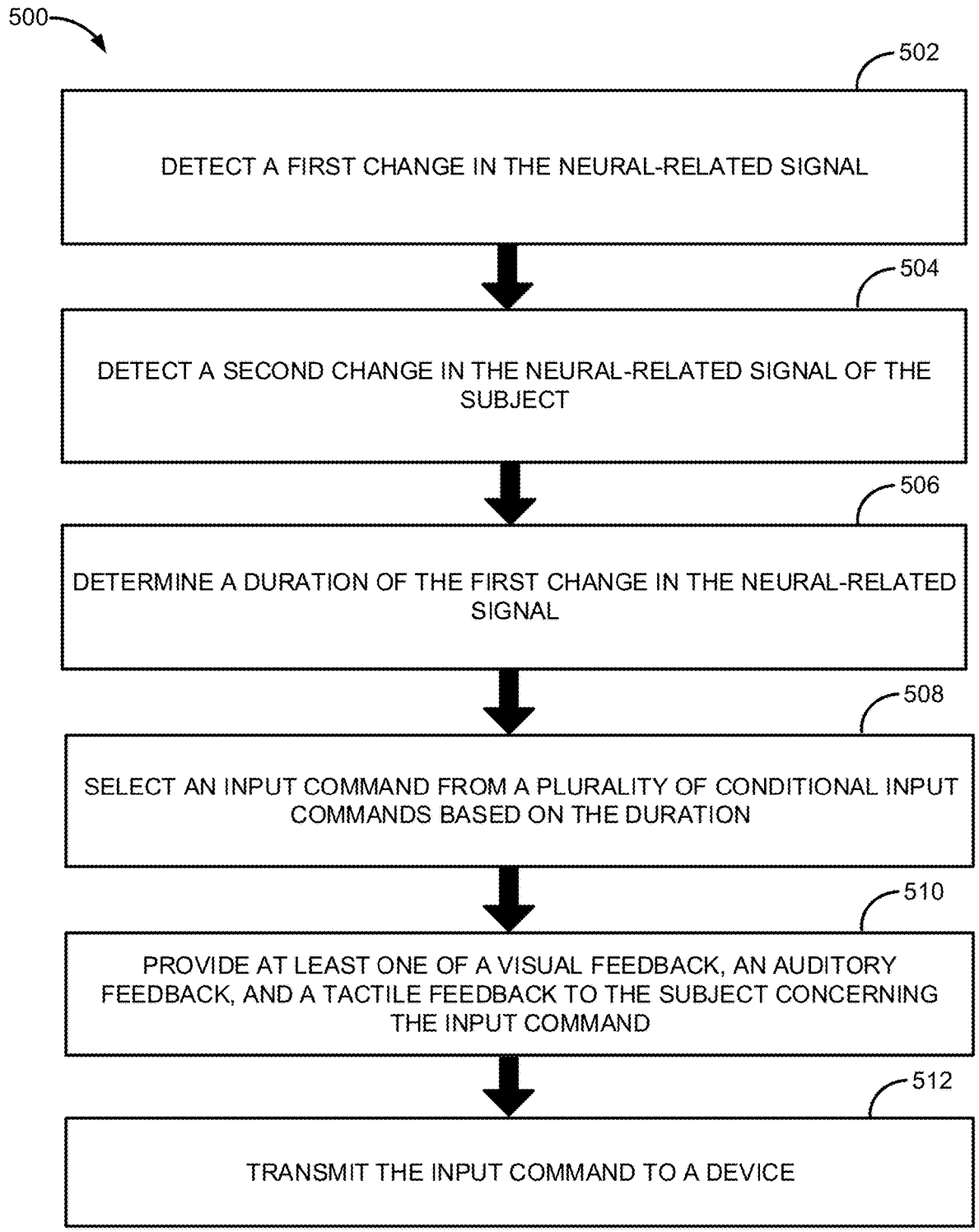
FIG. 13 illustrates yet another variation of a method for controlling a device or software using detected changes in a neural-related signal of a subject.

FIG. 13 illustrates another method 500 of controlling a device (e.g., a personal electronic device, an IoT device, a mobility vehicle, etc.), a software application (e.g., an end application 12), or a combination thereof using detected changes in a neural-related signal of a subject. The method 500 can comprise detecting a first change in the neural-related signal of the subject in operation 502. The method 500 can also comprise detecting a second change in the neural-related signal of the subject following the first change in operation 504.

In one embodiment, the first change in the neural-related signal can be a reduction in the intensity of the neural-related signal below a baseline signal level and the second change in the neural-related signal can be an increase in the intensity of the neural-related signal beyond the baseline signal level. For example, the first change in the neural-related signal can be a reduction in the power of a neural oscillation of the subject and the second change in the neural-related signal can be an increase in the power of the neural oscillation.

In this embodiment, the first change in the neural-related signal can be produced when the subject generates and holds a thought, such as a task-relevant thought or a task-irrelevant thought. The second change in the neural-related signal can be produced when the subject mentally releases the thought.

In an alternative embodiment, the first change in the neural-related signal can be an increase in the intensity of the neural-related signal above a baseline signal level and the second change in the neural-related signal can be a reduction or decrease in the intensity of the neural-related signal below the baseline signal level. For example, the first change in the neural-related signal can be an increase in the power of a neural oscillation of the subject and the second change in the neural-related signal can be a reduction or decrease in the power of the neural oscillation. More specifically, the first change in the neural-related signal can be an increase in the power of a gamma-band oscillation beyond a baseline gamma-band power level and the second change in the neural-related signal can be a decrease in the power of the gamma-band oscillation below the baseline gamma-band power level. In this embodiment, the first change in the neural-related signal (i.e., the increase in the power of the gamma-band oscillation) can be produced when the subject generates and holds a thought such as a task-relevant thought or a task-irrelevant thought. The second change in the neural-related signal (i.e., the decrease in the power of the gamma-band oscillation) can be produced when the subject mentally releases the thought.

In a further embodiment, the first change in the neural-related signal can be an increase in the intensity of a neural-related signal of a subject caused by the subject mentally releasing a first thought (e.g., a task-relevant thought or a task-irrelevant thought). In this embodiment, the second change in the neural-related signal can be a decrease in the intensity of the neural-related signal below the baseline signal level caused by the subject generating and holding a second or subsequent thought (e.g., another task-relevant thought or a task-irrelevant thought). The first thought, the second thought, or a combination thereof can be a thought related to a body function of the subject such as control of a muscle group of the subject. The input command 18 can be transmitted upon or following the subject generating the second thought.

The intensity changes can be detected using the neural interface 14 (e.g., via electrodes of the endovascular device implanted within the brain) and one or more processors of the telemetry unit 22, the host device 16, or a combination thereof.

The method 500 can further comprise determining a duration of the first change in the neural-related signal in operation 506. For example, when the neural-related signal is a neural oscillation of the subject, operation 506 can comprise determining the duration of a change in the power of the neural oscillation.

In some embodiments, the duration of the first change can be determined by calculating the elapsed time between a start of the first change and the start of the second change in the neural-related signal. For example, the duration can be elongated when the subject holds a thought (e.g., a task-relevant thought or a task-irrelevant thought) for a longer period of time.

In other embodiments, the duration of the first change can be determined by feeding samples or temporal segments of the subject's neural-related signal into a machine learning classifier (e.g., the machine learning classifier 308 of FIG. 11) and the machine learning classifier can classify the signal sample or signal bin as being in one of several pre-defined states (e.g., desynchronization state, rebound state, or rest state).

The method 500 can also comprise selecting an input command 18 from a plurality of conditional input commands based on the duration in operation 508. Selecting the input command 18 from the plurality of conditional input commands can further comprise comparing the duration with one or more temporal thresholds associated with the conditional input commands and selecting the input command 18 based on whether the duration exceeds or fails to reach the one or more temporal thresholds.

The method 500 can also comprise an optional operation 510 of providing a visual feedback, an auditory feedback, a tactile feedback, feedback in the form of neural stimulation, or a combination thereof to the subject concerning the input command 18 selected. For example, providing the visual feedback, the auditory feedback, the tactile feedback, the neural stimulation feedback, or a combination thereof can allow the subject an opportunity to confirm the input command 18 selected. In other embodiments, the feedback can be provided after transmitting the input command 18 to the device or software to inform the subject that the input command 18 has been transmitted or is in the process of being transmitted or carried out.

The method 500 can further comprise transmitting the input command 18 selected to the device or software in operation 512. In some embodiments, the input command 18 can be transmitted shortly after detecting the second change in the neural-related signal of the subject.

The input command 18 can be transmitted using one or more processors of the telemetry unit 22, the host device 16, or a combination thereof. As previously discussed, the input command 18 can be transmitted to one or more end applications (e.g., application software) run on a peripheral or personal computing device such as a laptop, a desktop computer, a smartphone, or a tablet computer. When the input command 18 is transmitted to a software program, the input command 18 can be transmitted via one or more software application programming interfaces (APIs). In these and other embodiments, the input command 18 can be transmitted to an IoT device, a mobility vehicle (such as an electric wheelchair), or other types of peripheral or personal computing devices to control such devices or vehicles. Moreover, the input command 18 can also be transmitted to one or more end applications (e.g., software) run on such peripheral or personal computing devices or vehicles.

One technical problem faced by the applicant is how to allow mobility-impaired patients (including patients with severe mobility limitations, such as locked-in patients) to control devices or software applications when such patients may only have control over their thoughts and/or certain muscle groups. One solution discovered by the applicant is to detect a first change (such as a reduction) in an intensity of a neural-related signal (e.g., a neural oscillation or brainwave) of the subject below a baseline level and detecting a second change (such as an increase) in the intensity of the neural-related signal beyond the baseline level following the first change and transmitting an input command to the device upon or following the detection in the second change of the neural-related signal. These changes can be detected using a neural interface implanted within a brain of the subject. This can allow a subject to control a device or software application by generating a thought (e.g., a task-relevant thought or task-irrelevant thought) and mentally releasing the thought.

Another technical problem faced by the applicant is which of the multitude of neural-related signals of the subject to monitor when a dependable and repeatable signal is needed to affect such control. One solution discovered by the applicant is to use neural oscillations of the subject including neural oscillations in the beta-band (about 12 Hz to 30 Hz), the gamma frequency range or gamma-band (about 30 Hz to 140 Hz, more specifically, 60 Hz to 80 Hz), the alpha frequency range or alpha-band (about 7 Hz to 12 Hz), the delta frequency range or delta-band (about 0.1 Hz to 3 Hz), the theta frequency range or theta-band (about 4 Hz to 7 Hz), or a combination thereof. Moreover, the neural-related signal can also comprise neural oscillations in the Mu band (about 7.5 Hz to 12.5 Hz), sensorimotor rhythm (SMR) band (about 12.5 Hz to 15.5 Hz), or a combination thereof.

Another technical problem faced by the applicant is how to allow mobility-impaired patients (including patients with severe mobility limitations, such as locked-in patients) to quickly and accurately control multiple devices or software applications. One solution discovered by the applicant is to select an input command from a plurality of conditional input commands based on a duration of a change in a neural-related signal of the subject (e.g., a decrease in the intensity of the neural-related signal). For example, the duration of the change in the neural-related signal can be calculated by classifying neural-related events (such as desynch events or rebound events) using a machine-learning classifier and comparing the number of such events with predetermined thresholds related to the conditional input commands. This can allow a subject to select among different commands by holding a thought (e.g., a task-relevant thought or a task-irrelevant thought) for a period of time and mentally releasing the thought when a threshold duration has been met.

FIG. 14 illustrates changes in the power of the beta-band (e.g., 12 Hz to 30 Hz) and gamma-band (e.g., 60 Hz to 80 Hz) frequencies as the subject conjures and holds and subsequently releases thoughts concerning movement of the subject's left and right ankles. As shown in FIG. 14, the power or intensity of the subject's neural oscillations in the beta-band can decrease when the subject generates and holds the thought and subsequently increase when the subject releases the thought. FIG. 14 also shows that the power or intensity of the subject's neural oscillations in the gamma-band can increase when the subject generates and holds a thought and subsequently decrease when the subject releases the thought. For example, the thoughts can be related to the subject attempting to move the subject's left ankle and right ankle.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method of controlling a device, comprising:
   detecting a reduction in an intensity of a neural-related signal of a subject below a baseline level measured, wherein the neural-related signal of the subject is a neural oscillation of the subject, and wherein detecting the reduction in the intensity of the neural-related signal comprises detecting a decrease in a power of the neural oscillation below a baseline oscillation power level, wherein the power is a power spectral density, wherein the reduction in the intensity of the neural-related signal is caused by the subject conjuring and holding a task-relevant thought;
   detecting an increase in the intensity of the neural-related signal beyond the baseline level following the reduction, wherein the increase in the intensity of the neural-related signal is caused by the subject mentally releasing the task-relevant thought; and
   transmitting an input command to the device upon or following the detection of the increase in the intensity of the neural-related signal, wherein the input command is a command to the device to accomplish at least part of a task associated with the task-relevant thought.

2. The method of claim 1, wherein detecting the increase in the intensity of the neural-related signal comprises detecting an increase in the power of the neural oscillation.

3. The method of claim 1, wherein the neural-related signal is measured or monitored using an endovascular device implanted within the subject, and wherein the steps of detecting the reduction or increase in the intensity of the neural-related signal and transmitting the input command are performed using one or more processors.

4. The method of claim 3, further comprising:
   filtering, using one or more processors of an apparatus implanted within the subject, raw neural-related signals obtained from the endovascular device using one or more software filters; and
   feeding filtered signals into a classification layer to automatically detect the reduction and increase in the intensity of the neural-related signal using a machine learning classifier.

5. The method of claim 1, wherein the reduction in the intensity of the neural-related signal below the baseline level measured is a desynchronization of the neural-related signal and wherein the increase in the intensity of the neural-related signal beyond the baseline level measured is a rebound of the neural-related signal.

6. A system for controlling a device, comprising:
an endovascular device configured to measure or monitor a neural-related signal of a subject, wherein the neural-related signal of the subject is a neural oscillation of the subject; and
an apparatus comprising one or more processors and wherein the one or more processors are programmed to:
detect a reduction in an intensity of the neural-related signal of a subject below a baseline level measured by detecting a decrease in a power of the neural oscillation below a baseline oscillation power level, wherein the power is a power spectral density, wherein the reduction in the intensity of the neural-related signal is caused by the subject conjuring and holding a task-relevant thought,
detect an increase in the intensity of the neural-related signal beyond the baseline level following the reduction, wherein the increase in the intensity of the neural-related signal is caused by the subject mentally releasing the task-relevant thought, and
transmit an input command to the device upon or following the detection of the increase in the intensity of the neural-related signal, wherein the input command is a command to the device to accomplish at least part of a task associated with the task-relevant thought.

7. The system of claim 6, wherein the one or more processors are programmed to detect the increase in the intensity of the neural-related signal by detecting an increase in the power of the neural oscillation beyond a baseline oscillation power level.

8. The system of claim 6, wherein the endovascular device is configured to be implanted within a vein or sinus of the brain of the subject.

9. The system of claim 6, wherein the one or more processors are further programmed to filter raw neural-related signals obtained from the endovascular device using one or more software filters.

10. The system of claim 9, wherein the one or more processors are further programmed to feed filtered signals into a classification layer to automatically detect the reduction and increase in the intensity of the neural-related signal using a machine learning classifier.

11. The system of claim 6, wherein the reduction in the intensity of the neural-related signal below the baseline level measured is a desynchronization of the neural-related signal and wherein the increase in the intensity of the neural-related signal beyond the baseline level measured is a rebound of the neural-related signal.

12. A method of controlling a device, comprising:
detecting a reduction in an intensity of a neural-related signal of a subject below a baseline level measured, wherein the neural-related signal of the subject is a neural oscillation of the subject, and wherein detecting the reduction in the intensity of the neural-related signal comprises detecting a decrease in a power of the neural oscillation below a baseline oscillation power level, wherein the power is a power spectral density, wherein the reduction in the intensity of the neural-related signal is caused by the subject conjuring and holding a task-irrelevant thought;
detecting an increase in the intensity of the neural-related signal beyond the baseline level following the reduction, wherein the increase in the intensity of the neural-related signal is caused by the subject mentally releasing the task-irrelevant thought; and
transmitting an input command to the device upon or following the detection of the increase in the intensity of the neural-related signal, wherein the input command is a command to the device to accomplish at least part of a task not associated with the task-irrelevant thought.

13. The method of claim 12, wherein detecting the increase in the intensity of the neural-related signal comprises detecting an increase in the power of the neural oscillation.

14. The method of claim 12, wherein the neural-related signal is measured or monitored using an endovascular device implanted within the subject, and wherein the steps of detecting the reduction or increase in the intensity of the neural-related signal and transmitting the input command are performed using one or more processors.

15. The method of claim 14, further comprising:
filtering, using one or more processors of an apparatus implanted within the subject, raw neural-related signals obtained from the endovascular device using one or more software filters; and
feeding filtered signals into a classification layer to automatically detect the reduction and increase in the intensity of the neural-related signal using a machine learning classifier.

16. The method of claim 12, wherein the task-irrelevant thought is a thought related to a body function of the subject.

17. The method of claim 12, wherein the reduction in the intensity of the neural-related signal below the baseline level measured is a desynchronization of the neural-related signal and wherein the increase in the intensity of the neural-related signal beyond the baseline level measured is a rebound of the neural-related signal.

18. A system for controlling a device, comprising:
an endovascular device configured to measure or monitor a neural-related signal of a subject, wherein the neural-related signal of the subject is a neural oscillation of the subject; and
an apparatus comprising one or more processors and wherein the one or more processors are programmed to:
detect a reduction in an intensity of the neural-related signal of a subject below a baseline level measured by detecting a decrease in a power of the neural oscillation below a baseline oscillation power level, wherein the power is a power spectral density, wherein the reduction in the intensity of the neural-related signal is caused by the subject conjuring and holding a task-irrelevant thought,
detect an increase in the intensity of the neural-related signal beyond the baseline level following the reduction, wherein the increase in the intensity of the neural-related signal is caused by the subject mentally releasing the task-irrelevant thought, and
transmit an input command to the device upon or following the detection of the increase in the intensity of the neural-related signal, wherein the input command is a command to the device to accomplish at least part of a task not associated with the task-irrelevant thought.

19. The system of claim 18, wherein the task-irrelevant thought is a thought related to a body function of the subject.

* * * * *